United States Patent [19]

Fujiyama et al.

[11] Patent Number: 5,455,777
[45] Date of Patent: Oct. 3, 1995

[54] METHOD OF PREDICTING DETERIORATION AND DAMAGE OF STRUCTURAL MEMBER AND PREDICTION APPARATUS FOR USE WITH THE METHOD

[75] Inventors: Kazunari Fujiyama; Itaru Murakami; Yomei Yoshioka; Nagatoshi Okabe, all of Yokohama, Japan

[73] Assignee: Kabushiki Kaisha Toshiba, Kawasaki, Japan

[21] Appl. No.: 154,543

[22] Filed: Nov. 19, 1993

[30] Foreign Application Priority Data

Nov. 20, 1992 [JP] Japan ................................. 4-312327

[51] Int. Cl.$^6$ ................................................ G06F 15/20
[52] U.S. Cl. ........................................... 364/507; 73/866.4
[58] Field of Search ........................ 73/799, 804, 866.4; 364/507, 508

[56] References Cited

U.S. PATENT DOCUMENTS

| | | | |
|---|---|---|---|
| 4,215,412 | 7/1980 | Bernier et al. | 364/431.02 |
| 5,159,563 | 10/1992 | Miller et al. | 364/507 |
| 5,210,704 | 5/1993 | Husseiny | 364/551.01 |

OTHER PUBLICATIONS

K. Fujiyama, et al., "Journal of the Gas Turbine Society of Japan", vol. 19, Mar. 1992, pp. 78–84.
H. L. Bernstein, "Life Assessment and Repair Technology for Combustion Turbine Hot Section Components", Apr. 17, 1990, pp. 111 to 118.

*Primary Examiner*—Hezron E. Williams
*Assistant Examiner*—Max Noori
*Attorney, Agent, or Firm*—Oblon, Spivak, McClelland, Maier & Neustadt

[57] ABSTRACT

An apparatus for predicting a deterioration and damage in a structural member of a prime mover or the like has a use condition monitoring unit for monitoring a condition of use of the structural member, an inspection unit for inspecting a deteriorated and damaged state of the structural member, a use condition setting unit for setting a use condition by being supplied with use condition data of the structural member from the use condition monitoring unit, a simulation unit for forming a model of the deterioration and damage in the structural member on the basis of the use condition of the structural member and a result of inspection of the structural member at a preceding time, and for simulating the advancement of the deterioration and damage in the structural member on the basis of the deterioration/damage model, and an inverse analysis unit for correcting a simulation model formed by the simulation unit by comparing the simulation model with a result of inspection of the structural member at the present time. The simulation unit is arranged to predict a future deterioration and damage in the structural member by using the corrected simulation model and the result of present inspection. By a deterioration/damage prediction apparatus of the invention using this apparatus, the deterioration and damage in the structural member can be accurately predicted using a simulation and an inverse-problem analysis method with respect to use conditions and results of inspection of the structural member, i.e., information actually available.

3 Claims, 32 Drawing Sheets

EQUI-STRESS LINE

CONCLUSION : USABLE UNTIL NEXT INSPECTION

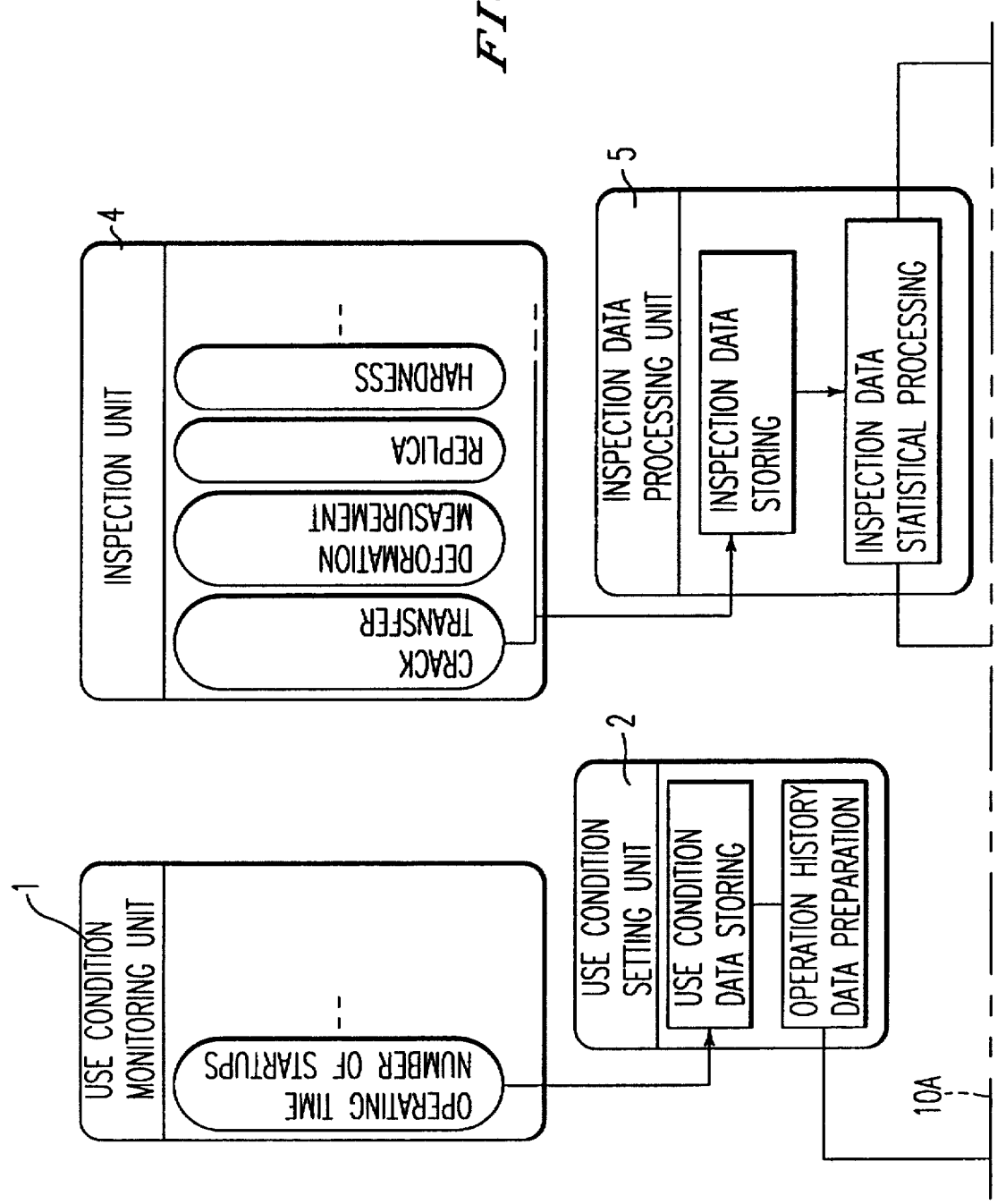

METHOD OF PREDICTING DETERIORATION AND DAMAGE OF STRUCTURAL MEMBER AND PREDICTION APPARATUS FOR USE WITH THE METHOD

BACKGROUND OF THE INVENTION

1. Field of the Invention

This invention relates to a method of predicting a future deteriorated and damaged state of a structural member of a prime mover or the like used under a severe condition, e.g., a member of a gas turbine or a jet engine, on the basis of used conditions and the result of inspection of the structural member, and to a prediction apparatus for use with the method.

2. Description of the Related Art

Recently, environments in which structural members of gas turbines and jet engines are used have become severer, and deterioration and damage in such structural members, typically in gas turbines for generating electric power, have become noticeable. Gas turbines recently developed are used under severe conditions such that main component parts, such as moving blades, stationary blades and combustors, are exposed to combustion gas at a high temperature exceeding 1,000° C., and the turbine is started and stopped frequently. Therefore, a deterioration due to a change with time and damage due to generation of cracks, voids, separation an the like in the structure of the materials of structural members of the gas turbines have become considerably large.

Conventionally, models for predicting a course of deterioration and damage in each of structural members of gas turbines have been proposed. For example, a conception of a cumulative damage law has been widely applied with respect to generation of cracks due to fatigue and creep.

An evaluation method based on the cumulative damage law is used as described below. As shown in FIG. 27, damage caused in a case where fatigue and creep have a complex effect is evaluated by performing temperature-stress analysis, using a material data bank, and correcting material characteristic data on the basis of an operation history and inspection. Creep damage $\Phi c$ and fatigue damage $\Phi f$ are calculated by the following equations:

$$\Phi c = t/tr, \quad \Phi f = n/Nf \tag{1}$$

where t: operating time tr: creep rupture time n: startup times

Nf: fatigue rupture times.

A creep-fatigue limit damage line shown in FIG. 27 is experimentally obtained from the combination of creep damage $\Phi c$ and fatigue damage $\Phi f$ at crack generation limits. This creep-fatigue limit damage line and the combination of creep damage $\Phi c$ and fatigue damage $\Phi f$ are compared to predict an accumulated state P1 and a future advanced state Pn of the damage.

Other methods in which the growth of a single macroscopic crack is predicted by destruction dynamics are now being used widely (which are, for example, a method proposed by Viswanathan in Damage Mechanics and Life Assessment of High-Temperature Components, ASM International, 1989, Chapter 1, pp 70–71, Chapter 6, p 301, Chapter 9 p 461, and a method described in Proceedings of International Conference on Life Assessment and Repair Technology or Combustion Turbine Hot Section Components, 1990, p 111).

The conventional methods are based on a conception that a deterioration and damage can be predicted if an initial state of a structural member is fixed and if a future operation prospect is determined. However, in a case where various kinds of deterioration and damage occur in a structural member under complex factors, the construction of a prediction model is very difficult and the advancement of deterioration and damage in the structural member is non-linear and depends largely upon the order of deterioration of potions of the structural member. Therefore, a small variation in an initial state may result in a large variation in the deteriorated and damaged state of the structural member. A multiplicity of thermal fatigue cracks can be observed in a stationary blade of a gas turbine as an example of damage to a structural member caused under complex factors. A phenomenon is known in which such thermal fatigue cracks grow complexly and synergistically, depending upon a temperature-stress distribution, a material structure distribution and interference between the cracks. A case where a deterioration and damage in a coating on a moving blades or the like of a gas turbine influence the advance of a deterioration and damage in a base member can be mentioned as an example of the problem relating to the order of deterioration and damage in a structural member. A method of predicting the advancement of damage under complex factors by simulation analysis (Nippon Gas Turbine Gakkai-shi, 19–76, 1992, p 78) has been proposed as a trial of damage prediction in such a case. However, deterioration and damage in structural members cannot always be predicted sufficiently by this method.

In the conventional methods for predicting a deterioration and damage in a structural member, it is difficult to construct a model of a deterioration and damage in the structural member if there are complex causes of the deterioration and damage or if the advancement of deterioration and damage is non-linear, and there is still a problem of how a prediction system is arranged to accurately predict the deteriorated and damaged state of a structural member in a case where the advancement of deterioration and damage cannot be correctly predicted.

SUMMARY OF THE INVENTION

In view of the above-described circumstances, an object of the present invention is to provide a method and apparatus for accurately predicting a deterioration and damage in a structural member by using a simulation and an inverse-problem analysis method with respect to use conditions and results of inspection of the structural member which are information actually available.

Another object of the present invention is to provide a method and apparatus for predicting the life of a structural member by accurately predicting a deterioration and damage in the structural member caused under complex factors.

To achieve these objects, according to one aspect of the present invention, there is provided a method of predicting a deterioration and damage in a structural member, comprising the steps of forming a model of the deterioration and damage in the structural member on the basis of a condition of use of the structural member and a result of inspection at a preceding time, forming a simulation model by simulating the advancement of the deterioration and damage in the structural member on the basis of the structural member deterioration/damage model, correcting the simulation model by comparing the simulation model with a result of inspection of the structural member at the present time, and predicting a future deterioration and damage in the structural member by using the corrected simulation model and the result of the present inspection of the structural member.

According to another aspect of the present invention, there is provided a method of predicting a deterioration and damage in a structural member, comprising the steps of converting a result of inspection of the structural member into a statistic of a deteriorated and damaged state of the structural member, setting an initial state of the deterioration and damage in the structural member on the basis of the statistic, and predicting a statistic of a future deteriorated and damaged state of the structural member from the initial state and a deterioration/damage advancement model by numerical analysis, wherein the deterioration/damage advancement model is used by being corrected so that the difference between the predicted statistic of the deteriorated and damaged state of the structural member at the time of present inspection assumed from a result of inspection of the structural member at a preceding time and the statistic of the deteriorated and damaged state of the structural member obtained from a result of the present inspection is minimum or least.

According to yet another aspect of the present invention, there is provided a method of predicting a deterioration and damage in a structural member, comprising the steps of converting a result of inspection of the structural member into a statistic of a deteriorated and damaged state of the structural member, determining an optimal approximation formula from a change in the statistic, and predicting a statistic of a future deteriorated and damaged state of the structural member by the optimal approximation formula, wherein the optimal approximation formula is used by being corrected so that the difference between the predicted statistic of the deteriorated and damaged state of the structural member at the time of present inspection assumed from the statistic of the deteriorated and damaged state and an operation history determined by results of inspection at preceding times and the statistic of the deteriorated and damaged state of the structural member obtained from a result of the present inspection is minimum or least.

According to still another aspect of the present invention, there is provided a method of predicting a deterioration and damage in a structural member, comprising the steps of forming a structure model by converting a structural form of constituents of the structural member into a model formed of a set of lattice points and by providing coordinate positions and factors determining the advancement of the deterioration and damage in the structural member as lattice point information, performing finite element dividing in correspondence with boundaries between different structural elements of the structure model, relating attributes of the structural elements to divided finite elements, analyzing deterioration/damage acceleration factors of the structural member such as the temperature and stress of the constituents of the structural member by the finite element method, adding an analysis result to the lattice point information of the structure model, and calculating and predicting a transition of the deteriorated and damaged state of the structural member by comparing the information with material resistances at the lattice points.

According to a further aspect of the present invention, there is provided an apparatus for predicting a deterioration and damage in a structural member for use in a prime mover or the like, comprising a use condition monitoring unit for monitoring a condition of use of the structural member, an inspection unit for inspecting a deteriorated and damaged state of the structural member, a use condition setting unit for setting a use condition by being supplied with use condition data of the structural member from the use condition monitoring unit, a simulation unit for forming a model of the deterioration and damage in the structural member on the basis of the use condition of the structural member and a result of inspection of the structural member at a preceding time, and for simulating the advancement of the deterioration and damage in the structural member on the basis of the deterioration/damage model, and an inverse analysis unit for correcting a simulation model formed by the simulation unit by comparing the simulation model with a result of inspection of the structural member at the present time, wherein the simulation unit is arranged to predict a future deterioration and damage in the structural member by using the corrected simulation model and the result of present inspection.

In accordance with the present invention, a condition of use of a structural member of a prime mover or the like is monitored by the use condition monitoring unit, a deteriorated and damaged state of the structural member is inspected by the inspection unit, and the simulation unit forms a model of a deterioration and damage in the structural member on the basis of the structural member use condition and the result of inspection at the preceding time, and simulates the deterioration and damage in the structural member on the basis of the deterioration/damage model. The simulation model made by the simulation unit is compared with the result of present inspection of the structural member by an inverse analysis unit to be corrected. The corrected model is sent to the simulation unit.

The simulation unit is arranged to predict a future deterioration/damage in the structural member by using the corrected simulation model and the present inspection result. It is therefore possible to construct a deterioration/damage model having a close similarity to the actual state by using the inspection result and by an inverse-problem analysis method and to accurately predict the deterioration and damage in the structural member, even if the deterioration/damage phenomena of the structural member are complicated and the construction of a deterioration/damage model is difficult.

Also, the apparatus is arranged so that the simulation model is corrected every time from the use condition of the structural member and the inspection result by using an inverse-problem analysis method, and a future deterioration/damage in the structural member is predicted by using the corrected simulation model and the present (latest) inspection result, even if the deterioration and damage in the structural member are caused under complex factors, e.g., a material structure factor, a temperature-stress distribution factor, an environmental corrosion factor and damage interference factor, such that the advancement of deterioration and damage is non-linear and complicated. The deterioration/damage prediction accuracy is thereby improved and, accordingly, the life of the structural member can be predicted with improved reliability.

DESCRIPTION OF THE PREFERRED EMBODIMENTS

Preferred embodiments of the present invention will be described below with reference to the accompanying drawings.

Figure 1:
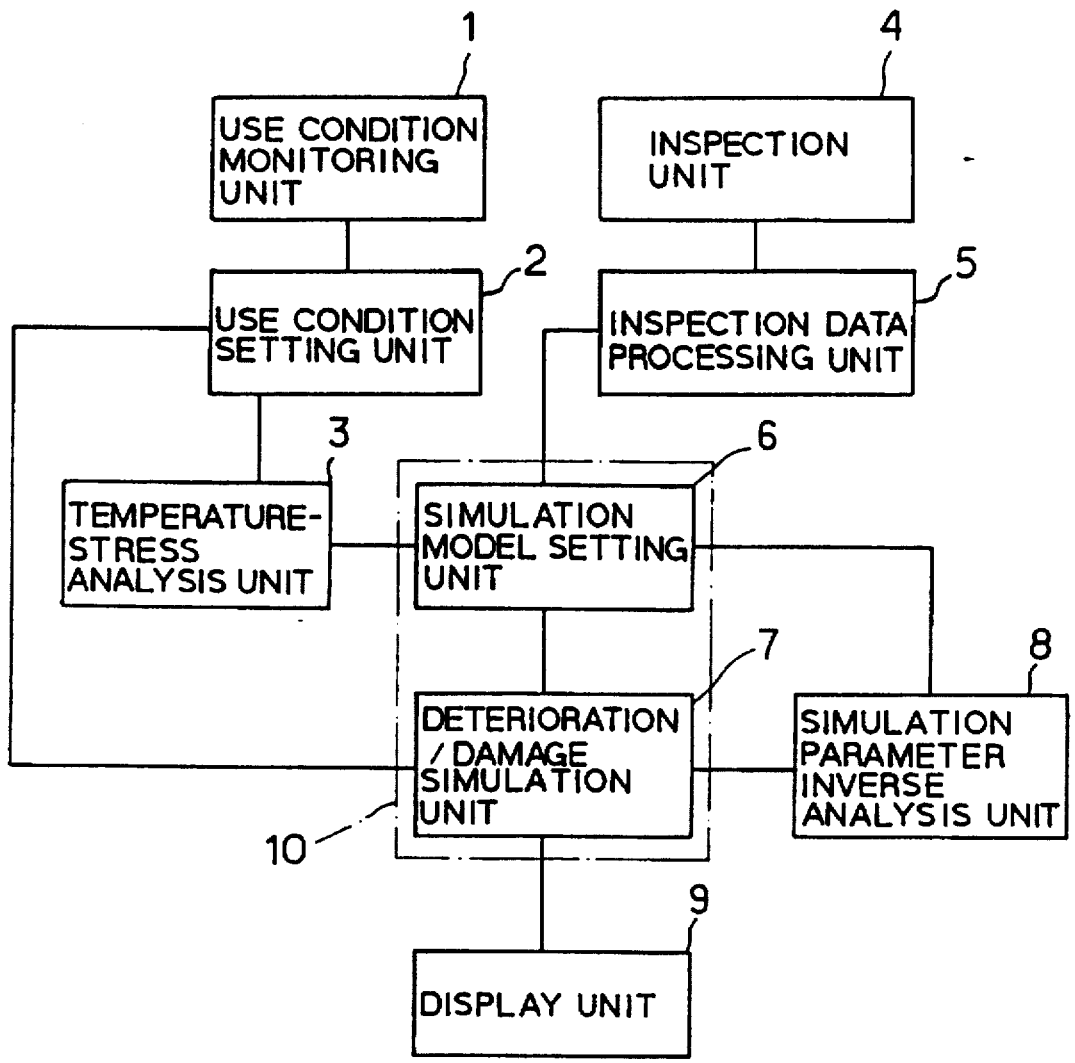
FIG. 1 is a diagram of the configuration of a basic apparatus for predicting a deterioration and damage in a structural member in accordance with an embodiment of the present invention.
Figure 2A:
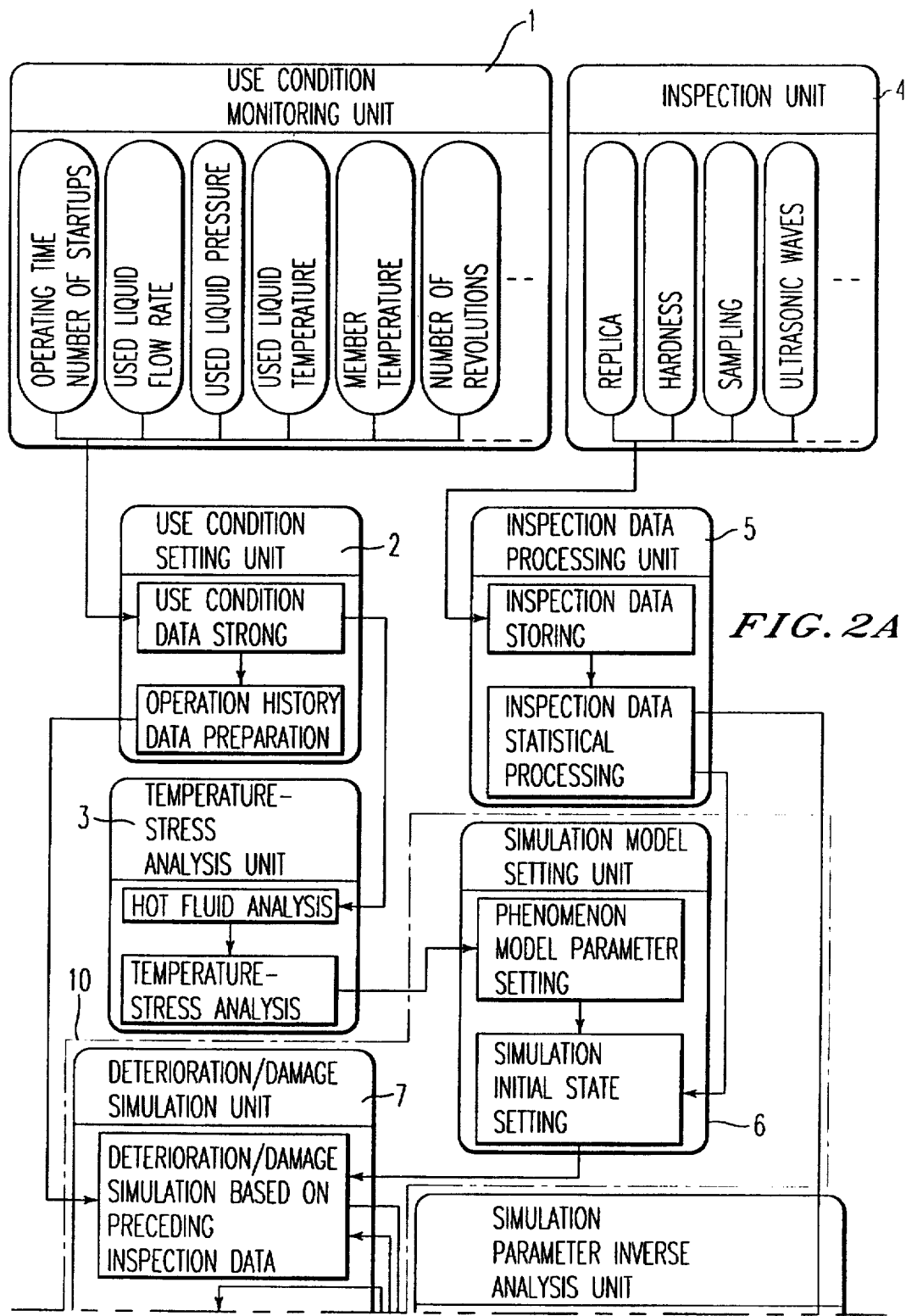
FIG. 2 is a diagram of the mutual relation between operations of the deterioration/damage prediction apparatus shown in FIG. 1.
Figure 2B:
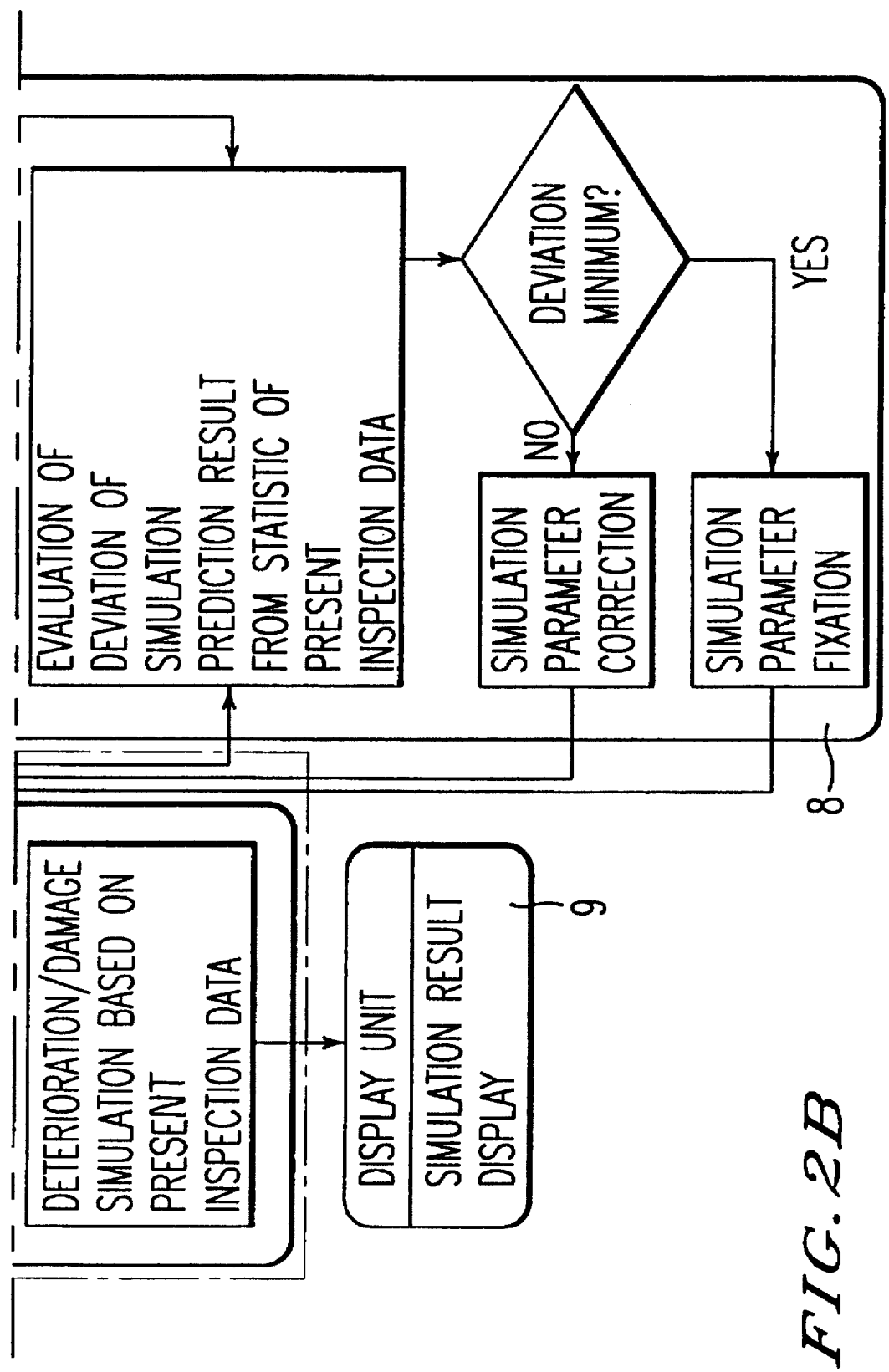

FIG. 1 is a diagram of the principle of an apparatus for predicting a deterioration and damage in a structural member in accordance with the present invention, and FIG. 2 is a diagram of the operation of the deterioration/damage prediction apparatus shown in FIG. 1. The deterioration/damage prediction apparatus serves to predict a change with time in a material structure and damage such as cracks, voids or separation in a structural member of a prime mover or the like used under a severe condition, e.g., a member of a gas turbine or a jet engine.

The deterioration/damage prediction apparatus has a use condition monitoring unit 1 for monitoring used conditions of the prime mover during operation. The use condition monitoring unit 1 is connected to a temperature-stress analysis unit 3 through a use condition setting device 2.

The use condition monitoring unit 1 detects signals representing various use conditions during operation, e.g., the operating time, the number of startups, the flow rate, pressure and temperature of a fluid used, the temperatures of portions of the prime mover structural member, and the number of revolutions, through various sensors attached to the structural member. The detected signals are stored as use condition data in the use condition setting unit 2. The use condition setting unit 2 prepares operation history data by relating the use condition data to the operating time and the number of startups to set conditions of use of the prime mover structural member.

On the other hand, the use condition data stored in the use condition setting unit 2 is sent to the temperature-stress analysis unit 3, in which hot fluid analysis is performed by using the finite element method or the boundary element method with the flow rate, pressure and temperature of the used fluid, the temperatures of the structural member portions and the number of revolutions among the use condition data used as boundary conditions, and in which temperature-stress analysis is performed on the basis of this hot fluid analysis.

An inspection unit 4, which measures the deterioration and damage in the prime mover structural member, is also provided. The inspection unit 4 is connected to a simulation model setting unit 6 through an inspection data processing unit 5.

For example, the inspection unit 4 observes the metallic structure of the structural member with a microscope by sampling a replica. The inspection unit 4 may also be arranged to measure a deteriorated and damaged state of the structural member by one of measuring the hardness of the structural member with a hardness tester, observing a sample with a microscope, measuring with ultrasonic waves or any other nondestructive measuring means, or by a combination of some of these operations. Inspection data relating to the measured deterioration and damage is supplied to the inspection data processing unit 5 and stored in the same. The inspection data processing unit 5 converts the inspection data into a statistic by optimally approximating the inspection data by statistical processing using a suitable distribution function form (using an optimal approximation formula). The statistic of the inspection data is sent to the simulation model setting unit 6.

The temperature-stress analysis unit 3 is connected to the simulation model setting unit 6 along with the inspection data processing unit 5. The simulation model setting unit 6 forms a model of the phenomenon of deterioration and damage in the structural member as a simulation object. For example, this deterioration/damage model is defined so that a resistance R to the deterioration and damage in the structural member and a deterioration/damage drive force F are adapted to deterioration/damage factors, e.g., a material structure factor, a temperature-stress distribution factor, an environmental corrosion factor and a damaging environment factor. In the defined model, rules of the deterioration and damage in the structural member are determined on the basis of physical laws of deterioration and damage.

For example, with respect to the generation and growth of a crack due to fatigue, the resistance R is a value of resistance of the material to the fatigue crack generation and growth, and the deterioration/damage drive force F is represented by the values of temperature and stress (strain) obtained in the temperature-stress analysis unit 3 or by a parameter obtained from the temperature and stress values (e.g., stress amplification coefficient K). An initial deteriorated and damaged state (deterioration/damage model) in a simulation model is set in the inspection data processing unit 5 so as to coincide statistically with the deteriorated and damaged state at the preceding inspection time obtained from the inspection unit 4.

The simulation model setting unit 6 is connected to a deterioration/damage simulation unit 7 along with the use condition setting unit 2. The deterioration/damage simulation unit 7 is connected again to the simulation model setting unit 6 through an inverse analysis unit, i.e., a simulation parameter inverse analysis unit 8, and is connected to a display unit 9. The simulation model setting unit 6 and the deterioration/damage simulation unit 7 form a simulator 10. The deterioration/damage simulation unit 7 simulates a future deterioration and damage by using the deteriorated and damaged state at the present inspection time as an initial state, and displays the result of the simulation through the display unit 9.

Thus, the advancement of deterioration and damage in the structural member is obtained by numerical simulation by using as an initial state the simulation model (deterioration/damage model) having the deteriorated and damaged state at the preceding inspection time set in the simulation model setting unit 6 on the basis of the operation history (the number of startups, the operating time, and so on) from the preceding inspection time to the present inspection time prepared in the use condition setting unit 2. Results of simulation are converted into a statistic by the same statistical processing as that of the inspection data processing unit 5. In the simulation parameter inverse analysis unit 8, a norm of the difference between the simulated deterioration/damage prediction statistic at the present inspection time (simulation model) and the statistic of the present inspection data obtained in the inspection data processing unit 5 is calculated as a deviation.

Next, the parameters of the simulation model are changed by the simulation parameter inverse analysis unit 8, deterioration/damage simulation at the present inspection time is performed on the basis of the preceding inspection data by the same procedure as that described above to make another simulation model, and a deviation of this simulation model from the present inspection result is calculated. When the deviation is minimized, the simulation parameters are fixed to form a corrected simulation model.

When the simulation parameters are fixed, future deterioration/damage simulation is performed by the deterioration/damage simulation unit 7 on the basis of the present inspection result and the corrected simulation model having the deteriorated and damaged state at the present inspection time as an initial state. The result of this simulation is displayed on the display unit 9.

This apparatus for predicting a deterioration and damage in a structural member is thus arranged to optimize a simulation model by successively performing inverse-problem analysis on the basis of conditions of use of a structural member of a prime mover or the like and the result of inspection, thus enabling a deterioration and damage in a structural member to be predicted accurately.

Figure 3:
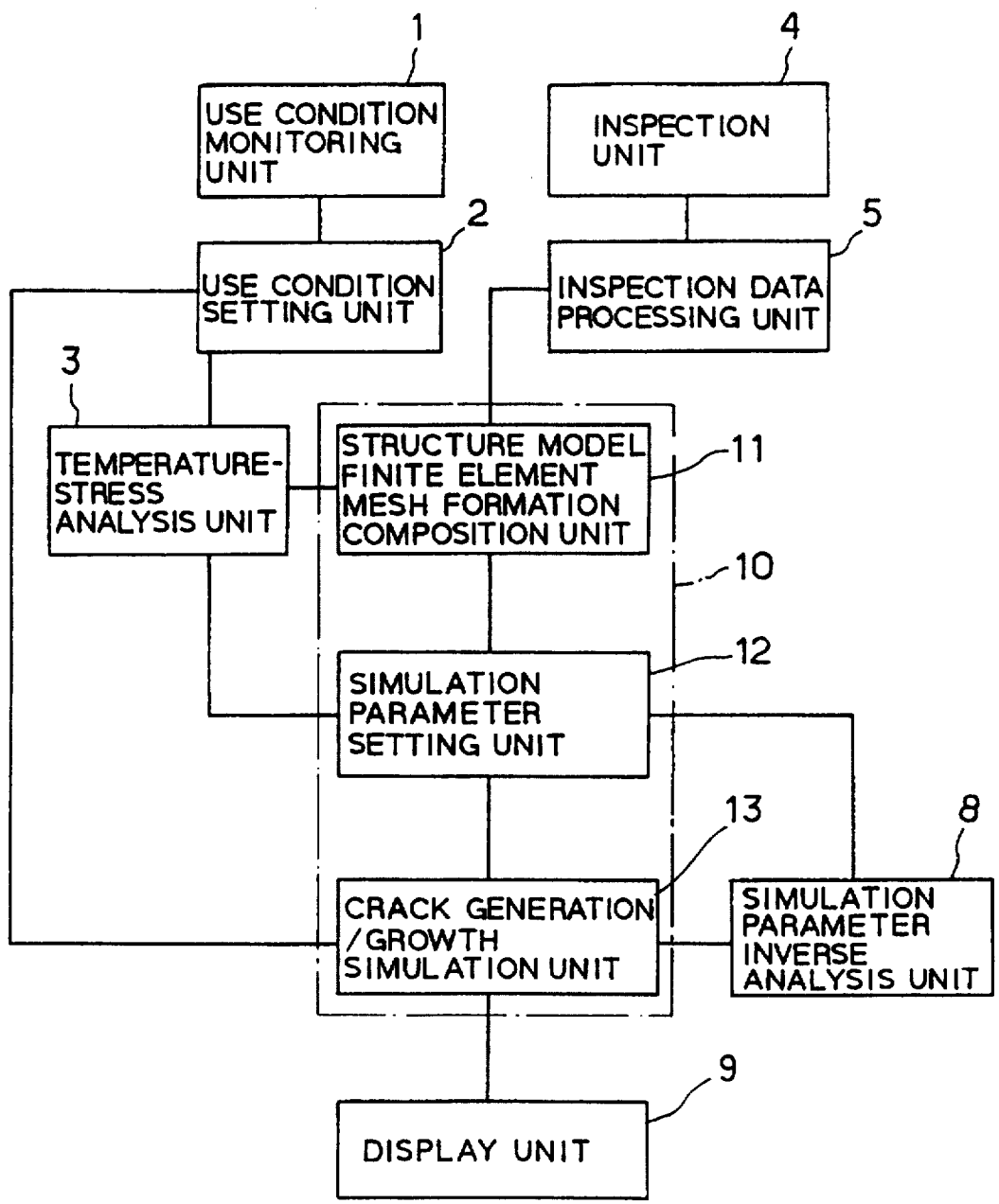
FIG. 3 is a diagram of the configuration of an apparatus for predicting a deterioration and damage in a structural member in accordance with a second embodiment of the present invention.
Figure 4A:
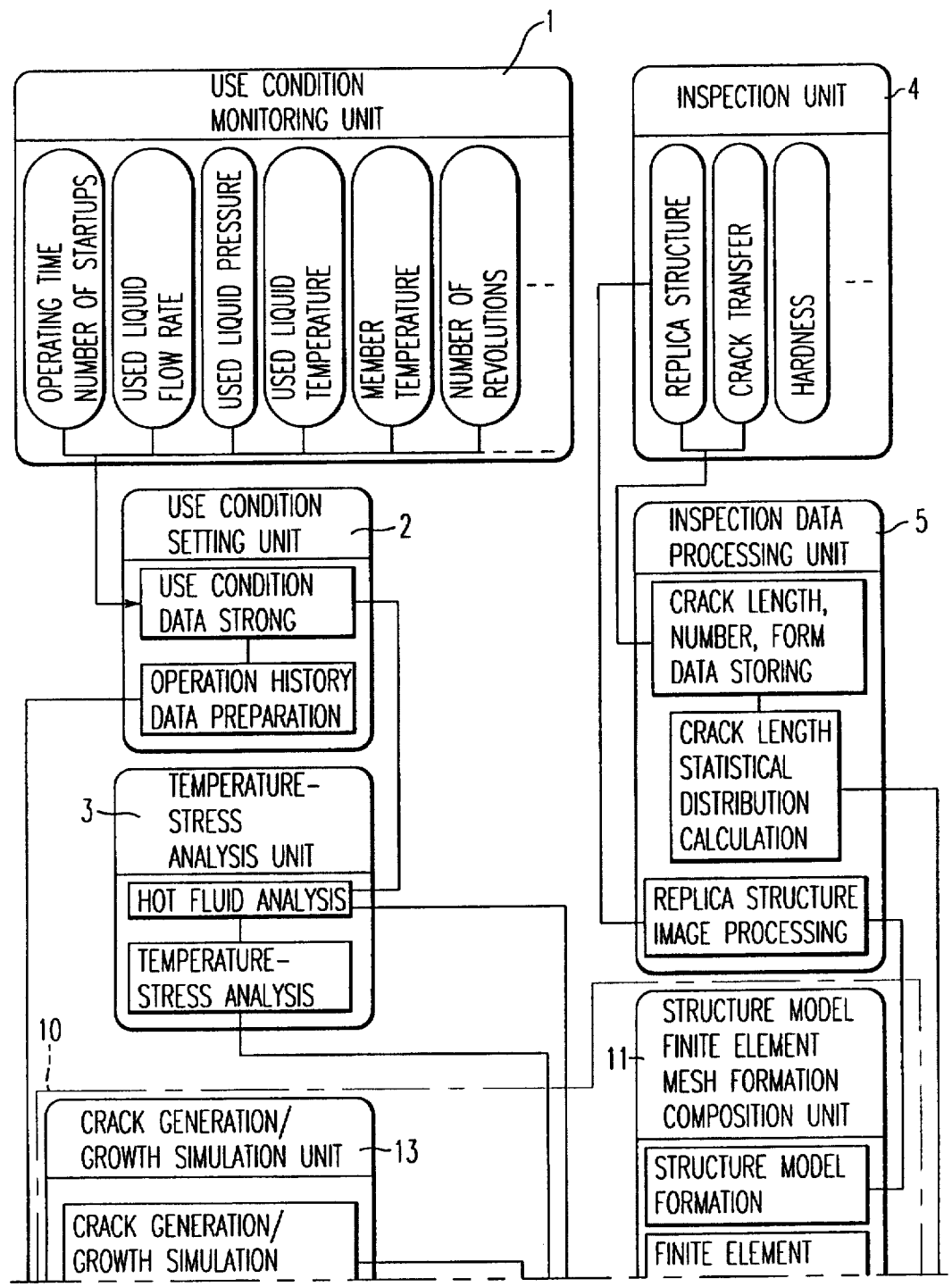
FIG. 4 is a diagram of the mutual relation between operations of the deterioration/damage prediction apparatus shown in FIG. 3.
Figure 4B:
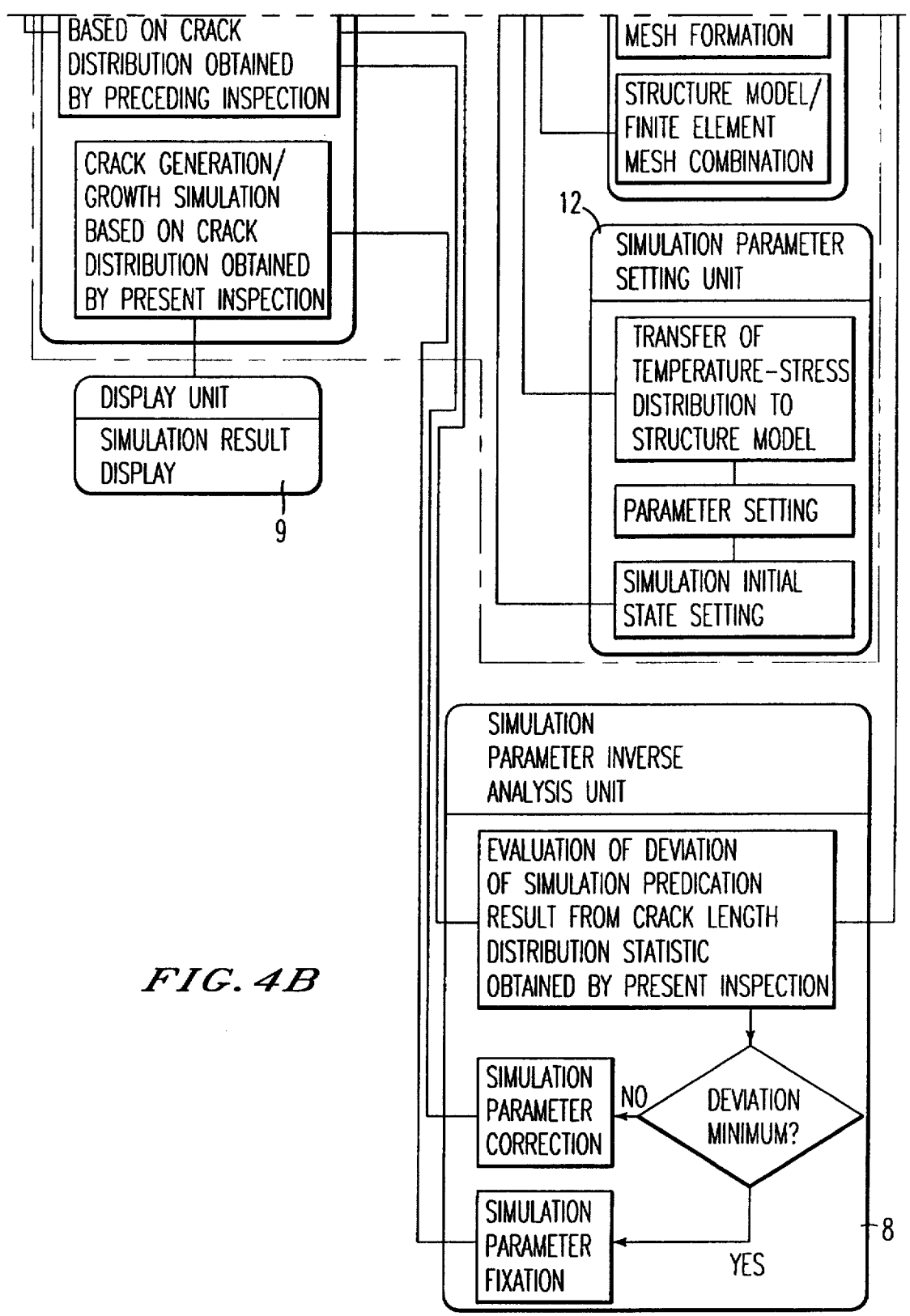

FIGS. 3 and 4 show a structural member deterioration/damage prediction apparatus in accordance with another embodiment of the present invention. In this deterioration/damage prediction apparatus, the structural member deterioration/damage prediction is applied to a prediction of a damaging phenomenon of generation and growth of fatigue cracks in a structural member.

For the description of the structural member deterioration/damage prediction apparatus, the same components as those of the apparatus shown in FIGS. 1 and 2 are indicated by the same reference characters. Basically, the structural member deterioration/damage prediction apparatus shown in FIGS. 3 and 4 differs from the deterioration/damage prediction apparatus shown in FIG. 1 in that it is provided with a structure model/finite element mesh formation/composition unit 11. This structural member deterioration/damage prediction apparatus has a use condition motoring unit 1 for monitoring conditions of use of a prime mover or the like, i.e., the operating time, the number or startups, the flow rate, temperature and pressure of a fluid used, and other factors, and an inspection unit 4 for inspecting and measuring a deterioration and damage in a structural member. The use condition monitoring unit 1 is connected to a temperature-stress analysis unit 3 through a use condition setting unit 2. An inspection data processing unit 5 is connected to the inspection unit 4. The inspection unit 4 is connected to the structure model/finite element mesh formation/composition unit 11 through the inspection data processing unit 5.

The structure model/finite element mesh formation/composition unit 11 is connected to the temperature-stress analysis unit 3 and to a simulation parameter setting unit 12. The temperature-stress analysis unit 3 is connected to the simulation parameter setting unit 12. The structure model/finite element mesh formation/composition unit 11 and the simulation parameter setting unit 12 correspond to the simulation model setting unit 6 shown in FIG. 1 and have similar functions.

The use condition setting unit 2 and the simulation parameter setting unit 12 are connected to a crack generation/growth simulation unit 13. The crack generation/growth simulation unit 13 is connected again to the simulation parameter setting unit 12 through an inverse analysis unit, i.e., a simulation parameter inverse analysis unit 8. The crack generation/growth simulation unit 13 corresponds to the deterioration/damage simulation unit 7 shown in FIG. 1 and is connected to a display unit 9 as in the case of the simulation unit 7.

The operation of this structural member deterioration/damage prediction apparatus will be described with reference to FIG. 4.

The structural member deterioration/damage prediction apparatus detects various conditions of use of a structural member of a prime mover or the like during operation through various sensors attached to the structural member. That is, signals representing various use conditions, e.g., the operating time, the number of startups, the flow rate, pressure and temperature of a fluid used, the temperatures of portions of the structural member, and the number of revolutions are detected and monitored by the use condition monitoring unit 1. The detected use condition signals are stored as use condition data in the use condition setting unit 2. The use condition setting unit 2 prepares, as operation history data, a history with respect to the operating time and the number of startups and so on of the use condition data.

Specifically, in this embodiment, the inspection unit 4 measures fatigue cracks and a metallic structure among various factors of deterioration and damage in the structural member. To do so, microscopic observation of a metallic structure and cracks and macrographic transfer of cracks through a replica are performed. A hardness measurement may be performed as one of means for measuring a metallic structure deterioration.

Figure 5:
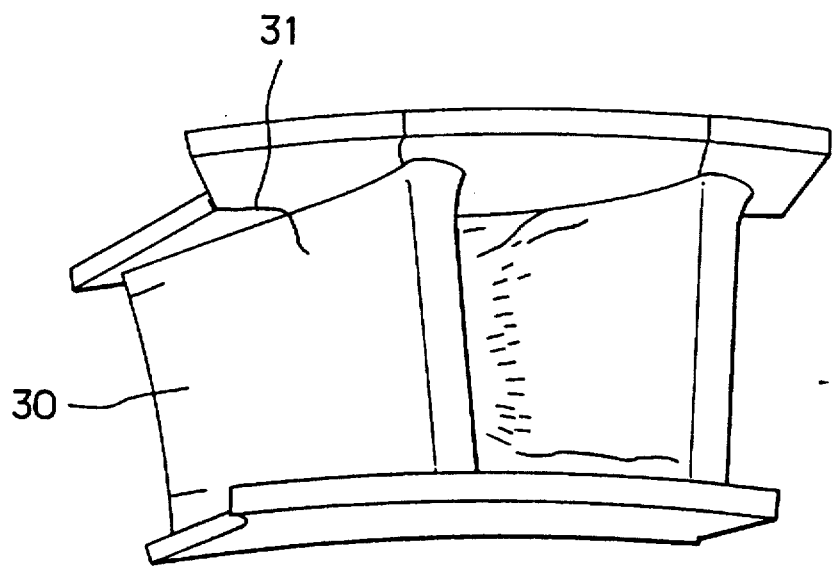
FIG. 5 is a schematic diagram of a situation where thermal fatigue cracks have occurred in a stationary blade which is a structural member of a gas turbine.
Figure 6:
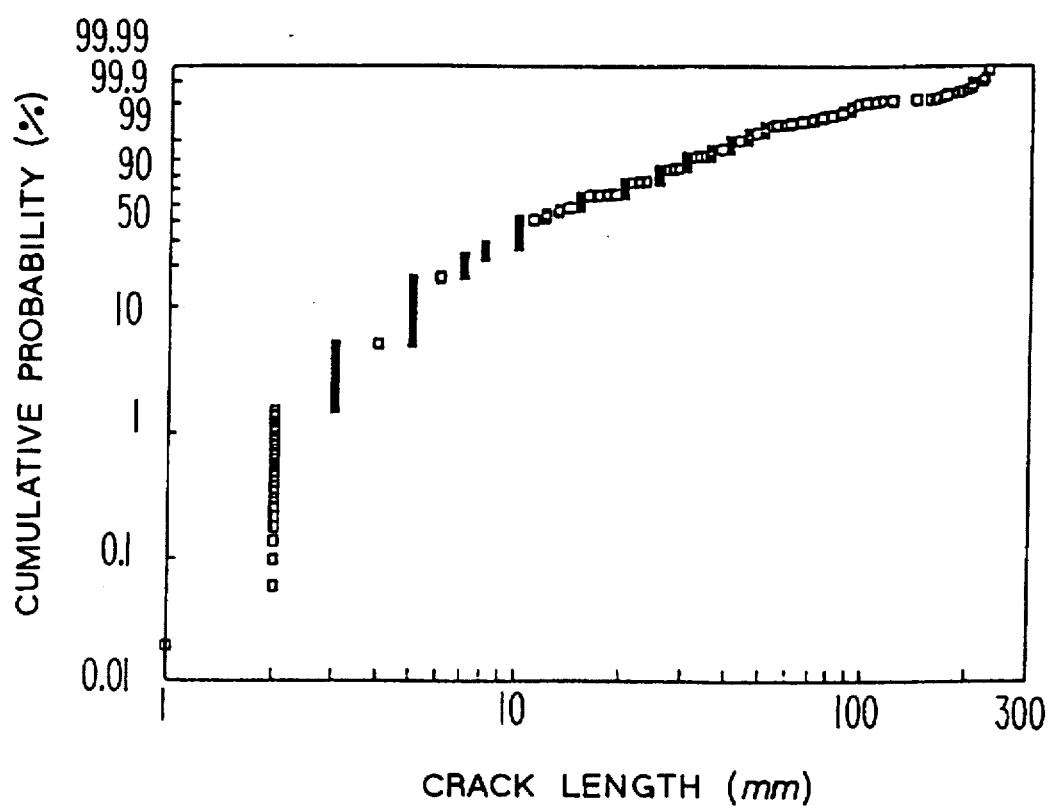
FIG. 6 is a diagram of a statistically-processed result of crack length inspection of the gas turbine stationary blade.

The length, the number and the form (designating a crack at a crystal boundary or a crack in a crystal grain) of cracks measured by the inspection unit 4 are stored and converted into statistics by statistical processing in the inspection data processing unit 5. In the case of a structural member shown in FIG. 5, i.e., a gas turbine stationary blade 30, a multiplicity of thermal fatigue cracks 31 are generated and grown during use, and the lengths of cracks 31 can be statistically processed, as shown in FIG. 6. In FIG. 6, thermal fatigue crack lengths are put in order as an order statistic from a small value to a large value and plotted in a Weibull chart, and can be approximated by a three-parameter Weibull distribution expressed by the following equation:

$$F(a)=1-\exp[\{(a-\gamma)/\beta\}^{\alpha}] \quad (2)$$

where

F(a): cumulative probability of crack length $\alpha$, $\beta$, $\gamma$: constants.

Figure 7:
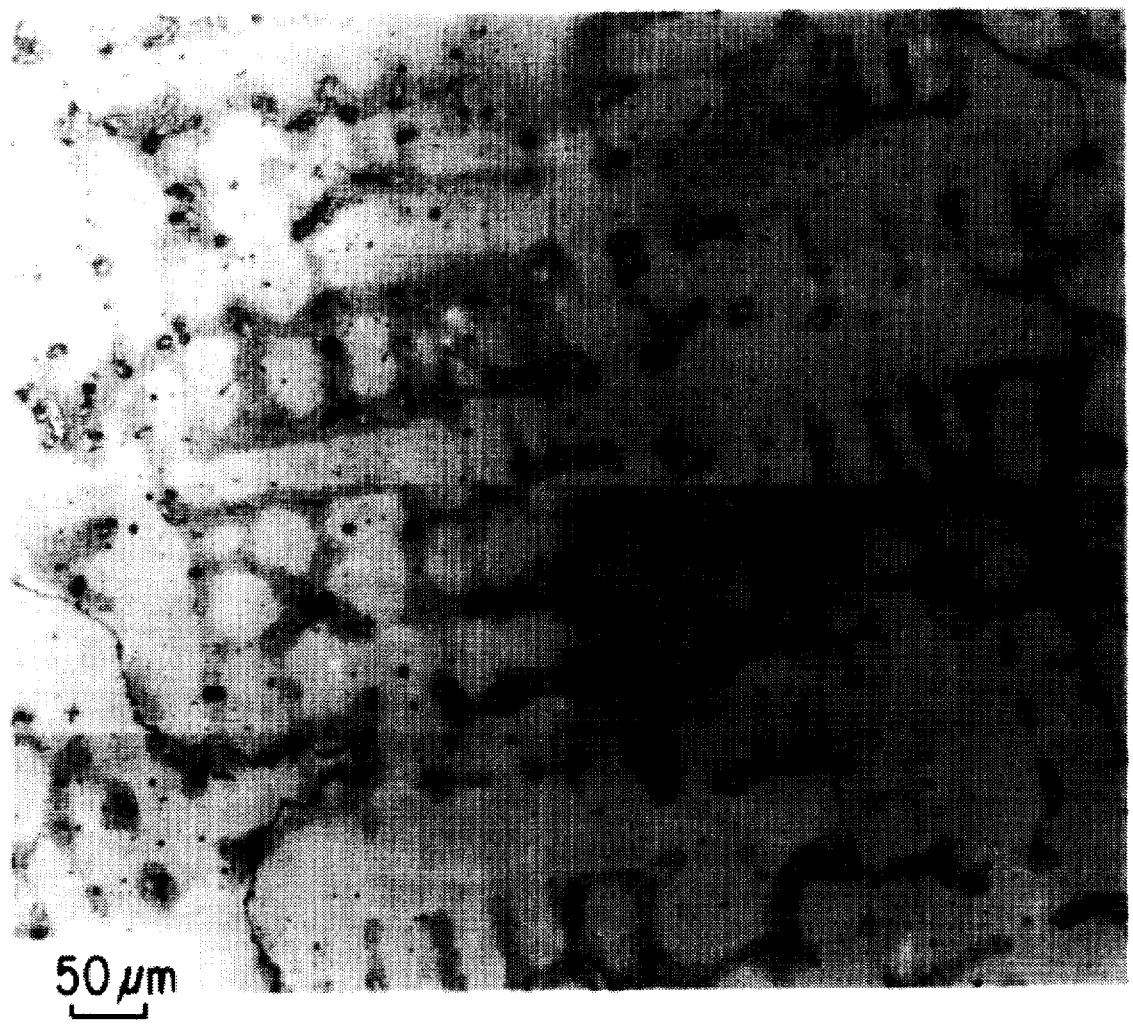
FIG. 7 is a microscopic photograph of a state of the metallic structure of the gas turbine stationary blade.

Referring again to FIG. 4, in the inspection data processing unit 5, a metallic structure image obtained by observing a replica with a microscope is changed into numerical data by an image processor. For example, a super alloy precision-cast material of the gas turbine stationary blade material exhibits a black-and-white random dendritic pattern, such as that shown in FIG. 7, in a microscopic photograph. The ratio of black and white structure areas is calculated as a parameter representing a structural form.

Figure 8:
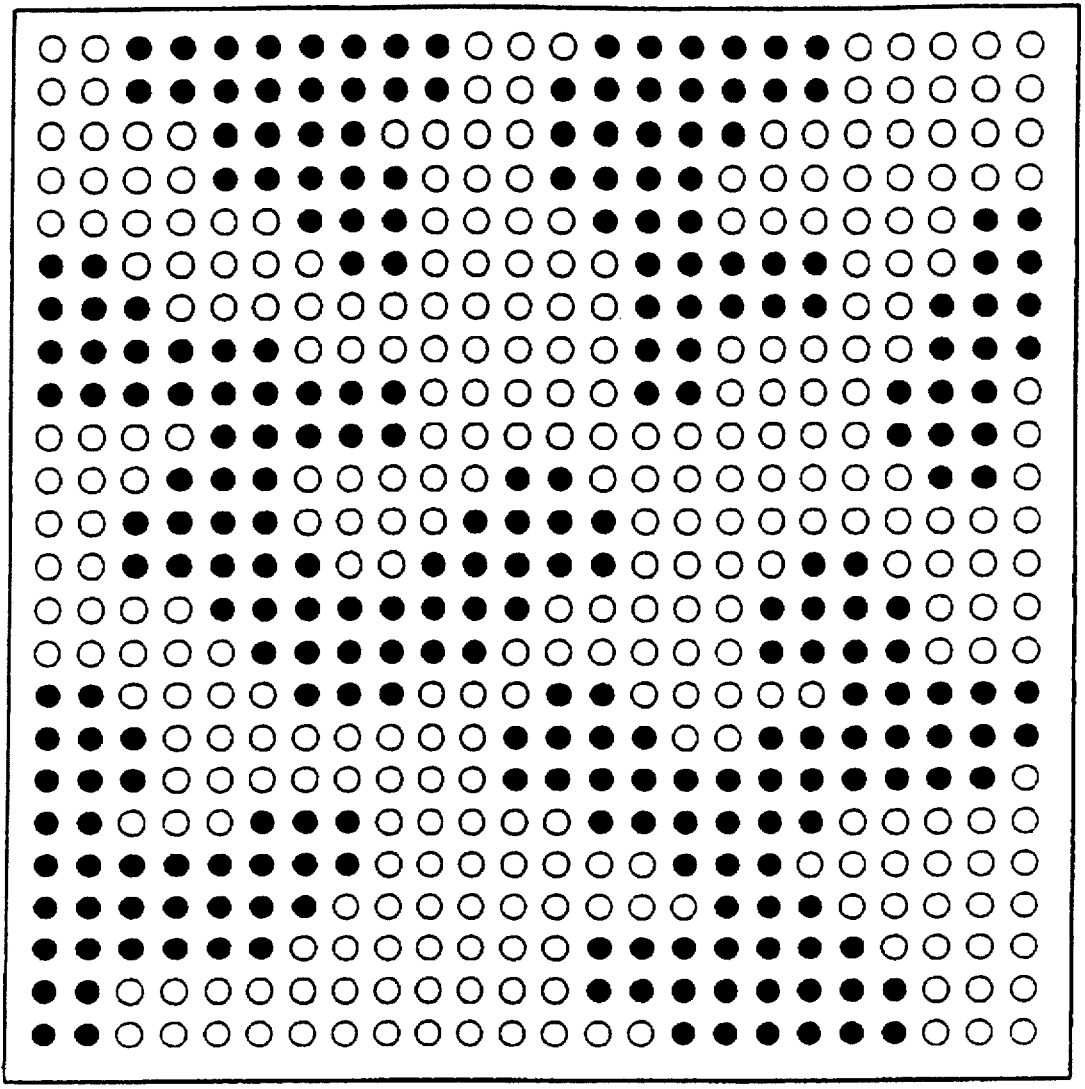
FIG. 8 is a diagram of an example of a structure model formed as a set of lattice points on an evaluation object region of the structural member.

On the other hand, a structure model is formed in the structure model/finite element mesh formation/composition unit 11. To form a metallic structure model, a model of an evaluation object region of the object structural member is first formed as a set of lattice points, that is, the object is represented by a lattice point set model, as shown in FIG. 8. If the object is a metallic structure formed of two phases as in the case of a gas turbine stationary blade material, two types of, i.e., black and white lattice points are distributed in accordance with the probability corresponding to the value of the structure area ratio obtained in the inspection data processing unit 5 by using random numbers.

Each lattice point does not designate one atom but designates a set of atoms of a particular element having a certain size, i.e., a cluster. To the cluster at each lattice point, material characteristics (heat transfer coefficient, heat conductivity, elastic constant, Poisson's ratio, and other factors) necessary for hot fluid analysis and temperature-stress analysis described below are given with respect to different phases of the material.

Figure 9:
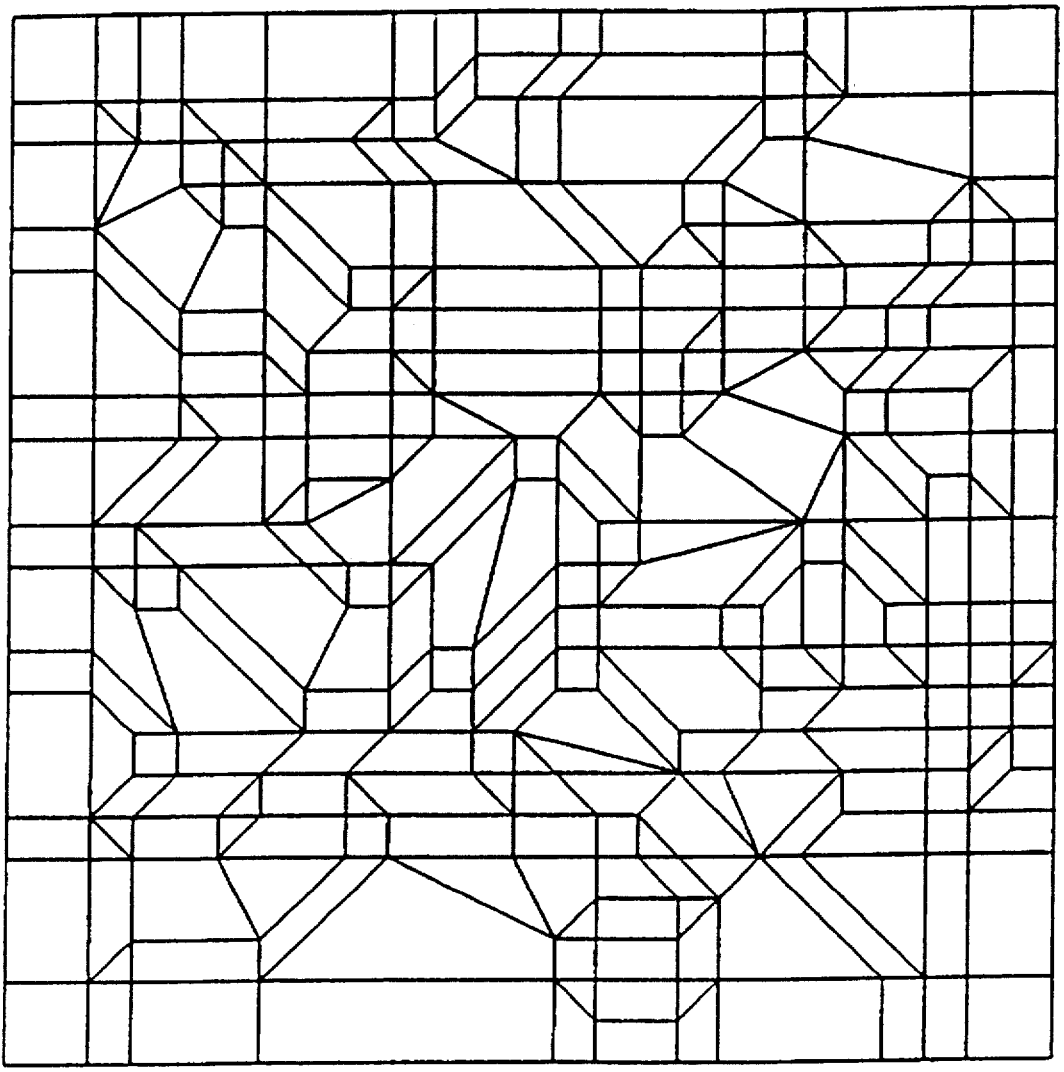
FIG. 9 is a diagram of meshes of finite elements for stress analysis, forming a finite element model of the evaluation object region of the structural member corresponding to the structure model.
Figure 10:
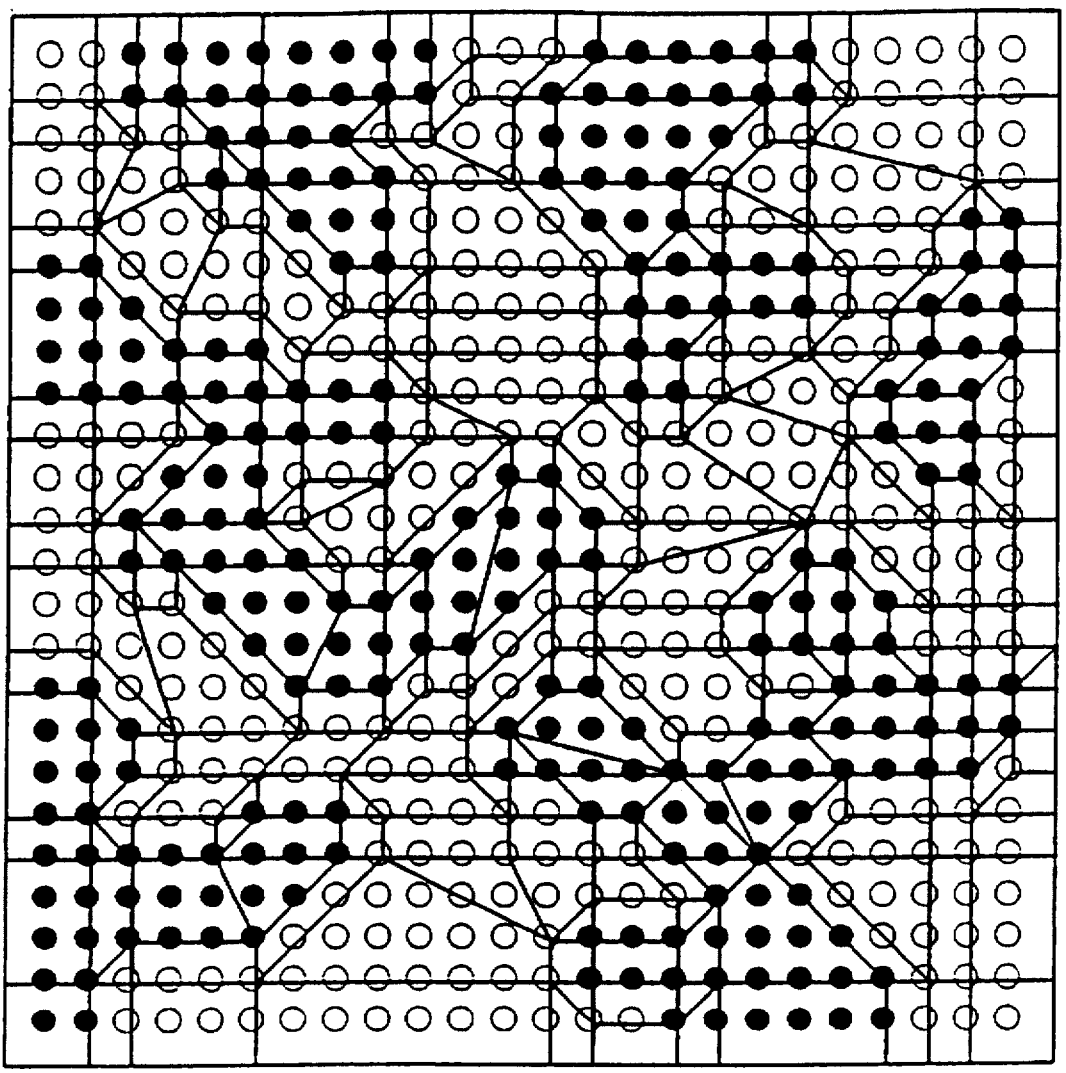
FIG. 10 is a diagram of a state in which the structure model and the finite element meshes are superposed on each other.
Figure 11:
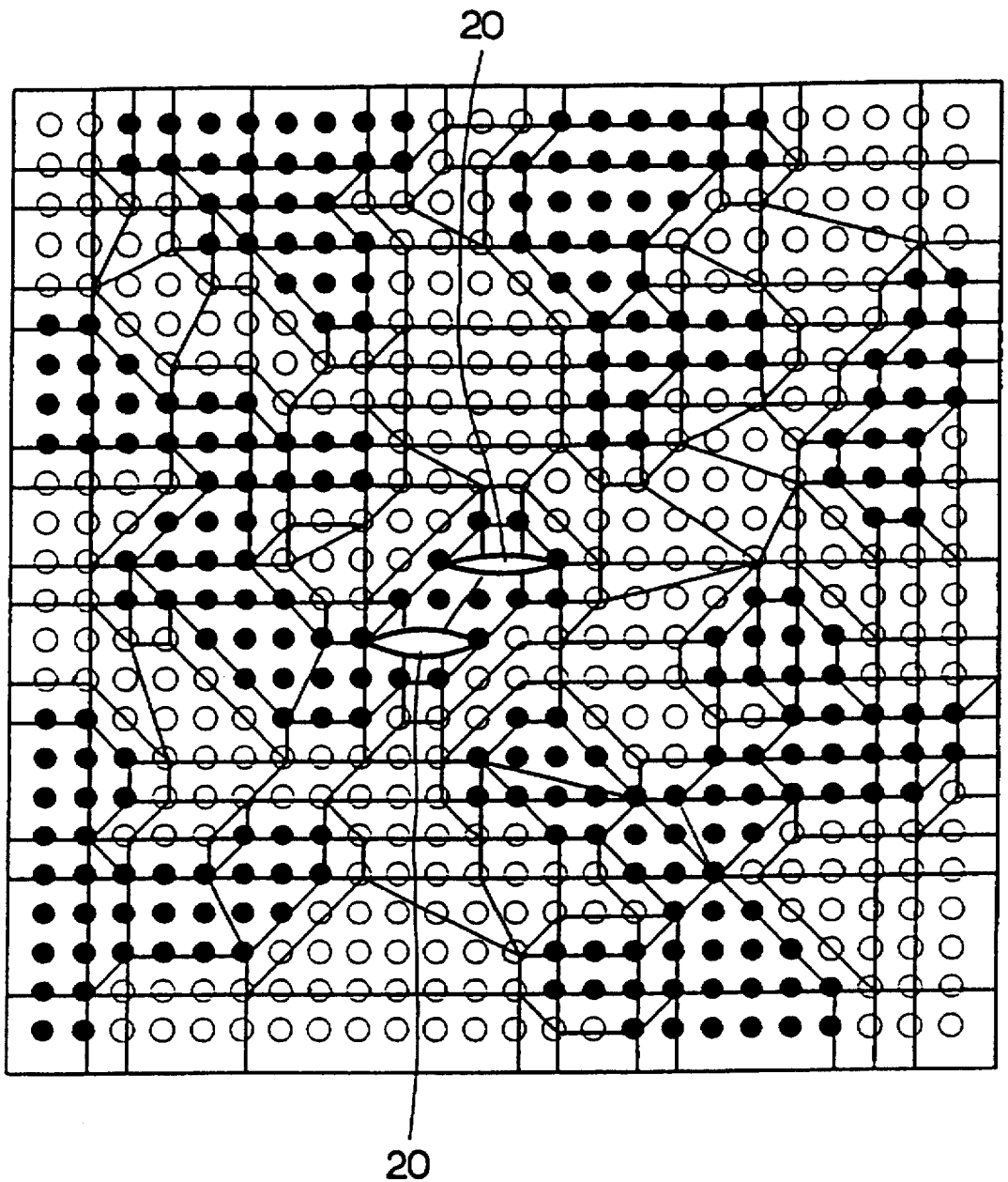
FIG. 11 is a diagram of a state in which the structure model and the finite element meshes are superposed on each other and in which cracks are introduced.

Next, finite element dividing is performed by forming finite element meshes, such as that shown in FIG. 9, having configurations in accordance with the boundaries between the phases of the structure model obtained as shown in FIG. 8. FIG. 10 shows the result of superposition of the metallic structure model and the finite element meshes. The material characteristics given to the lattice points are provided as information on the finite element meshes to combine the metallic structure model and the finite element meshes, thereby forming the structure model. If cracks exist previously in the structural member in an initial state, cracks 20 are distributed to finite element meshes as shown in FIG. 11 by a method described later.

Figure 12:
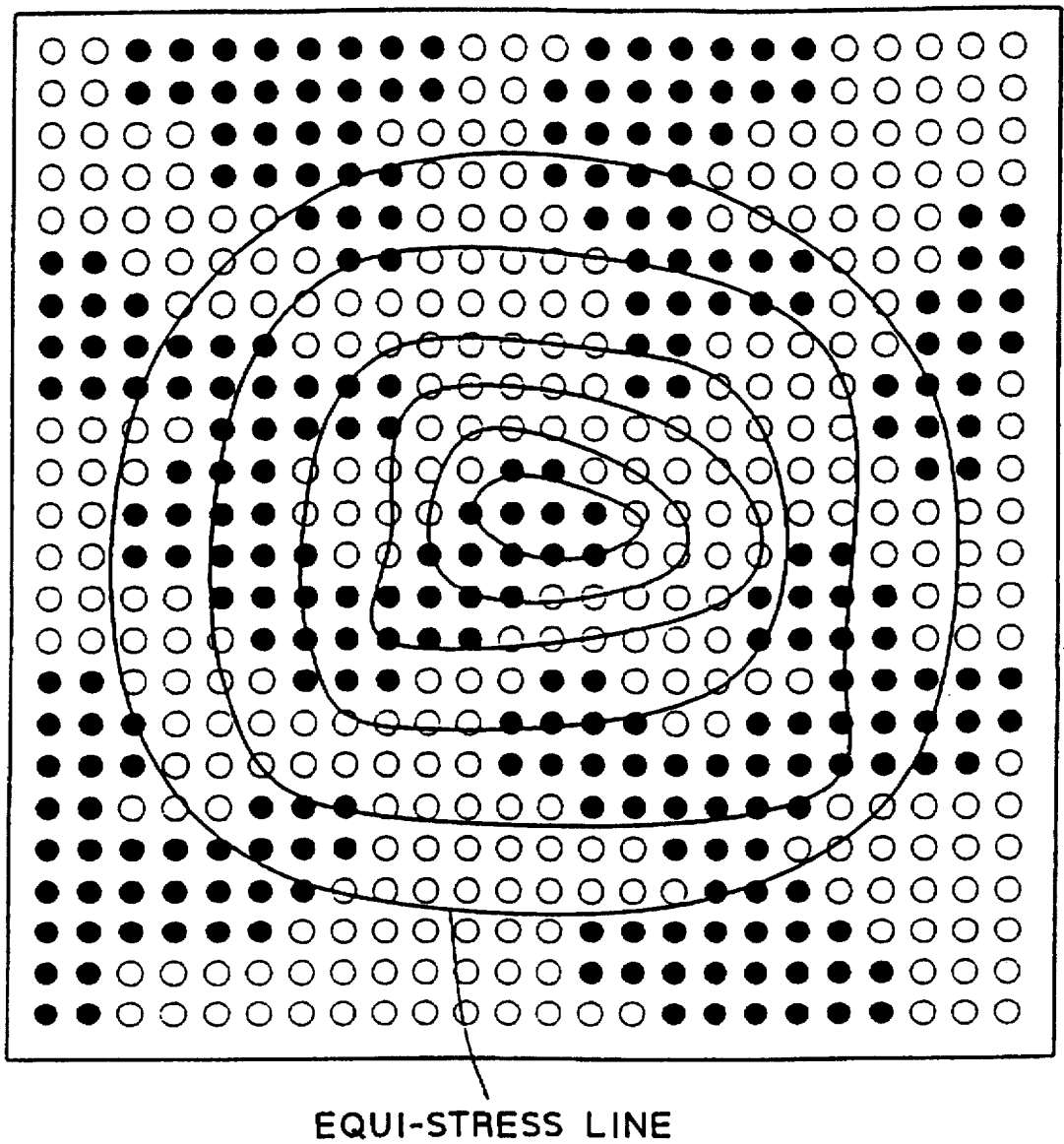
FIG. 12 is a diagram in which a stress distribution is related to the structure model.

In the temperature-stress analysis unit 3, the structure-finite element composition model obtained as described above is used to analyze deterioration/damage acceleration factors of the structural member through hot fluid analysis and temperature-stress analysis by the finite element method on the basis of the use condition data from the use condition setting unit 2. By this analysis, temperature-stress data is given to integral points of each finite element. In the simulation parameter setting unit 12, with respect to each integral point of the finite element meshes of the structure-finite element composition model, the temperature-stress values at the integral point are related to a lattice point included in a region surrounded by bisectors of adjacent integral points. In this manner, a temperature-stress distribution is obtained on the lattice points on the structure model, as shown in FIG. 12.

Next, resistance R of the material against the generation and growth of cracks and a parameter relating to crack generation/growth drive force F, such as the temperature-stress distribution obtained from the temperature-stress analysis unit 3, are assumed. A crack generation resistance RI and a crack growth resistance RG, which are material resistances, cannot be set as single constants because they are influenced by various composite factors. At this stage, therefore, supposed values are set.

An initial state of the crack distribution in a simulation model is set by using random numbers so as to coincide with the statistical distributions of the length and the number of cracks at the preceding time obtained by the inspection data processing unit 5. That is, the equation (2) is solved with respect to a to obtain $$a=\beta[\log\{1-F(a)\}^{-1}]^{1/\alpha}+\gamma \quad (3)$$

the cumulative probability F(a) of the crack length is given from random numbers to set a crack length distribution, and the positions of cracks 20 are randomly determined from random numbers, thereby setting an initial state of the model (deterioration/damage model), as shown in FIG. 11.

On the other hand, crack generation/growth is determined by numerical simulation on the basis of the operation history (the number of startups, the operating time, and so on) from the preceding inspection time to the present inspection time prepared in the use condition setting unit 2 by using the simulation model (deterioration/damage model) having as an initial state the crack distribution at the preceding inspection time set by the simulation parameter setting unit 12. In this simulation, the generation and Growth of cracks are subject to a damage function D represented by the following equations:

Crack Generation $D_{I,i} = D_{I,i-1} + \partial D_I (R, F)/\partial t \cdot \Delta t$ (4)

Crack Growth $D_{G,i} = D_{G,i-1} + \partial D_G (R, F)/\partial t \cdot \Delta t$ (5)

where $D_{I,i}$: Crack generation damage function at i stage $D_{G,i}$: Crack growth damage function at i stage t: time or number of times $\Delta t$: an increase in time or number of times between from i−1 stage to i stage $D_I (R,F) = 1 - \exp(-t/b_I)^{m_I}$ $b_I = R_I/F_I$ $D_G (R, F) = 1 - \exp(-t/b_G)^{m_G}$ $b_G = R_G/F_G$.

Simulation is performed and a simulation model is made by assuming that the values of the damage function D calculated at the lattice points by these equations are equal to the probabilities of occurrence of the crack generation/growth phenomenon.

In the simulation parameter inverse analysis unit 8, the crack length distribution is converted into a statistic by the equation (2) from the state of crack distribution prediction at the present inspection time obtained by the above-described simulation, and the difference between the values of constants $\{\alpha_S, \beta_S, \gamma_S\}$ of the converted values and present inspection data $\{\alpha_I, \beta_I, \gamma_I\}$ obtained in the inspection data processing unit 5 is calculated as a deviation.

That is, constants $\{\delta\alpha, \delta\beta, \delta\gamma\}$ are expressed by $\{\delta\alpha, \delta\beta, \delta\gamma\} = \{\alpha_S - \alpha_I, \beta_S - \beta_I, \gamma_S - \gamma_I\}$ (6)

$W(R, F, D) = \Sigma\{\omega_1 \cdot \delta\alpha^2 + \omega_2 \cdot \delta\beta^2 + \omega_3 \cdot \delta\gamma^2\}$ (7)

where $\Sigma$: sum in each simulation $\omega_1, \omega_2, \omega_3$: weighting functions.

Figure 13A:
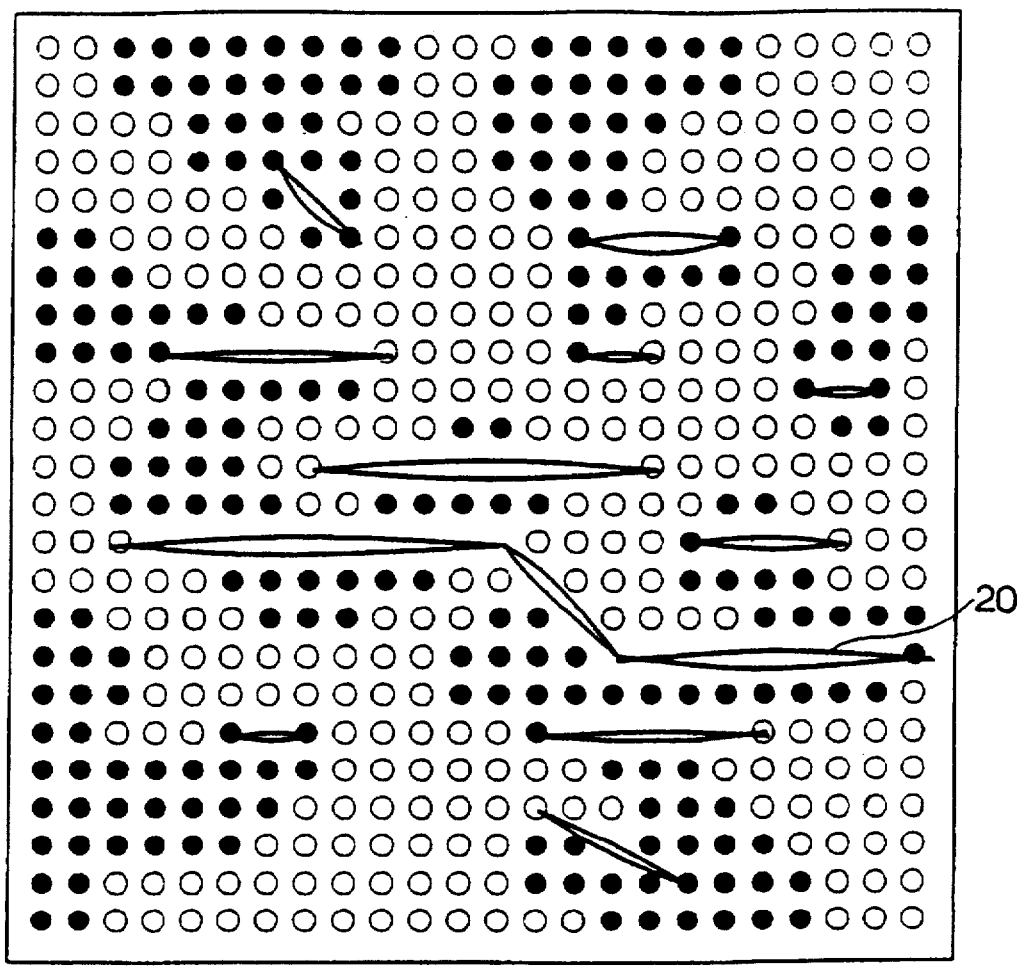
FIGS. 13(A) and 13(B) are schematic diagrams of occurrence of cracks in the structural member and prediction of growth of the cracks.
Figure 13B:
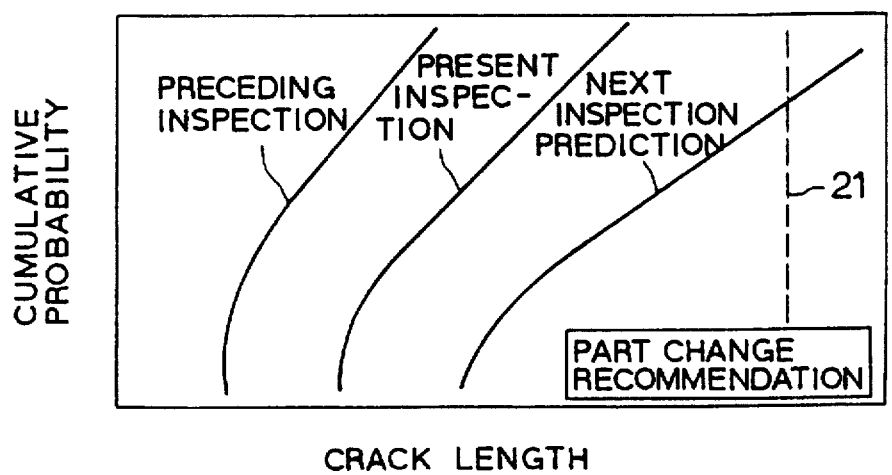

R, F and D such that the function W (R, F, D) of the damage parameters is minimum or least are searched for and obtained by repeated calculations, and corresponding parameter values are fixed as final values to form a corrected simulation model.

when the simulation parameters are fixed, future crack generation/growth simulation is performed by the crack generation/growth simulation unit 12 using the corrected simulation model having the crack distribution state at the present inspection time as an initial state. The result of this simulation is displayed on the display unit 9. FIGS. 13(A) and 13(B) show examples of display on the display unit 9. An image of the crack distribution obtained by simulation as shown in FIG. 13(A) and changes in crack length distribution such as those shown in FIG. 13(B) are displayed on the display unit 9. With respect to the crack length distribution changes, an allowable limit 21 is simultaneously indicated and a guidance for taking necessary measures, e.g., recommendation to repair or change the part is also shown.

This structural member deterioration/damage prediction apparatus is arranged to perform simulation analysis of a deterioration and damage, e.g., the generation and growth of cracks, in a structural member based on finite element analysis combined with a metallic structure model of the structural member. This simulation analysis is schematically illustrated in FIGS. 14(A) to 14(E).

In this structural member deterioration/damage prediction apparatus, a metallic structure model is formed from an evaluation object region of a structural member as a set of lattice points. The randomness of a structural distribution of the formed metallic structure model is expressed by the existence/non-existence of dots. Actually, it is represented by two types, i.e., black and white lattice points, as shown in FIG. 8.

Figure 14A:
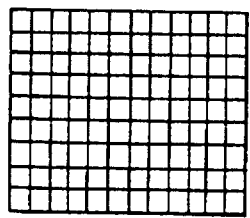
FIGS. 14(A) to 14(E) are schematic diagrams of the operation of the structural member deterioration/damage prediction apparatus of the present invention.
Figure 14B:
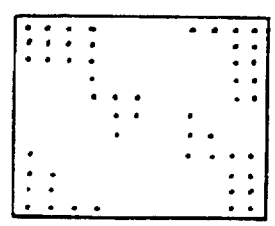
Figure 14C:
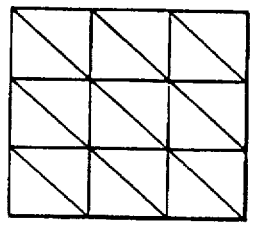
Figure 14D:
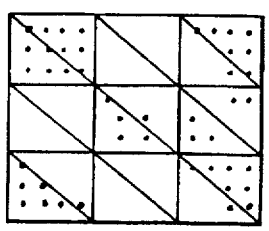
Figure 14E:
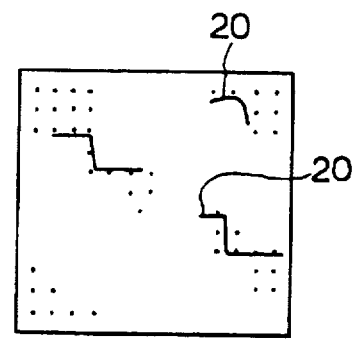

On the other hand, a finite element model of the evaluation object region of the structural member is formed, hot fluid analysis and temperature-stress analysis are performed with this model, and meshes of the finite element method (corresponding to FIG. 9) are formed. The metallic structure model of FIG. 14(B) is superposed on the meshes of the finite element method (finite element meshes) formed a shown in FIG. 14(C) to attach stress information to the dots of the metallic structure model as shown in FIG. 14(D). The metallic structure model and the finite element meshes can be combined by setting representative stresses of the meshes of the finite element method as stresses at the dots included in the evaluation object region and representing the material structure. By this combination, deterioration/damage analysis of the structural member in which a stress distribution and a material characteristic distribution are reflected, as shown in FIG. 14(E).

This structural member deterioration/damage prediction apparatus can optimize a deterioration/damage model by suitably using an inverse-problem analysis method and inspection results to accurately predict a deterioration and damage in a structural member even if factors which determine the advancement of the deterioration and damage are complicated or non-linear so that the construction of a deterioration/damage prediction model is difficult.

In short, this structural member deterioration/damage prediction apparatus converts a structural form of constituents of a structural member into a lattice point set model, attach coordinate positions and factors determining the advancement of a deterioration and damage in the structural member as lattice point information to form a structure model, performs finite element dividing in correspondence with the boundaries between different structural elements of this structure model, relates attributes of the structural elements to the divided finite elements, analyzes deterioration/damage acceleration factors of the structural member such as the temperature and stress of the constituents by the finite element method, adds an analysis result to the information on the structure model, compares the information with the material resistances at the lattice points to calculate and predict a transition of the deteriorated and damaged state of the structural member, and displays the result of the calculation and prediction on the display unit 9.

Figure 15:
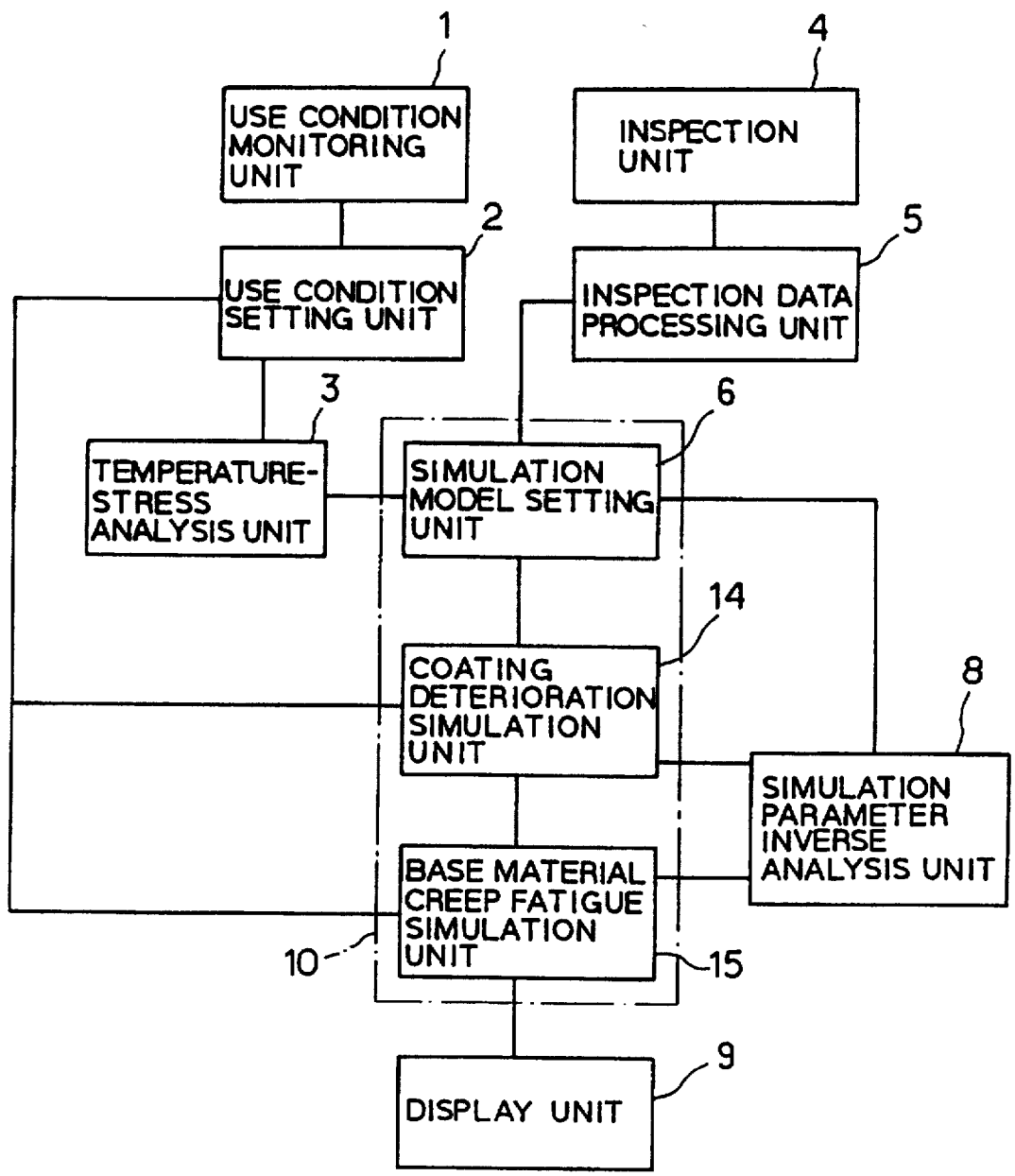
FIG. 15 is a diagram of the configuration of a structural member deterioration/damage prediction apparatus in accordance with a third embodiment of the present invention, showing an example of an application to a coated structural member.

FIG. 15 shows a structural member deterioration/damage prediction apparatus in accordance with a third embodiment of the present invention. The deterioration/damage prediction apparatus of this embodiment represents an example of an application of the present invention to a prediction of deteriorated phase generation due to diffusion of Al in a coated Ni-base super alloy member formed as a structural member. For the description of this embodiment, the same components as those of the deterioration/damage prediction apparatus described as the first embodiment are indicated by the same reference characters.

As shown in FIG. 15, the structural member deterioration/damage prediction apparatus has a use condition motoring unit 1 for monitoring conditions of use of a prime mover or the like, and an inspection unit 4 for inspecting a deterioration and damage in a structural member.

The use condition monitoring unit 1 is connected to a temperature-stress analysis unit 3 through a use condition setting unit 2. An inspection data processing unit 5 is connected to the inspection unit 4. The temperature-stress analysis unit 3 and the inspection data processing unit 5 are connected to a simulation model setting unit 6.

The simulation model setting unit 6 is connected to a coating deterioration simulation unit 14 and to a simulation parameter inverse analysis unit 8. The coating deterioration simulation unit 14 is connected to the use condition setting unit 2 and to a base material creep/fatigue simulation unit 15. The simulation units 14 and 15 and the simulation model setting unit 6 form a simulator 10.

The coating deterioration simulation unit 15 and the base material creep/fatigue simulation unit 15 are connected again to the simulation model setting unit 6 through the simulation parameter inverse analysis unit 8. The simulation units 14 and 15 are connected to a display unit 9.

Figure 16A:
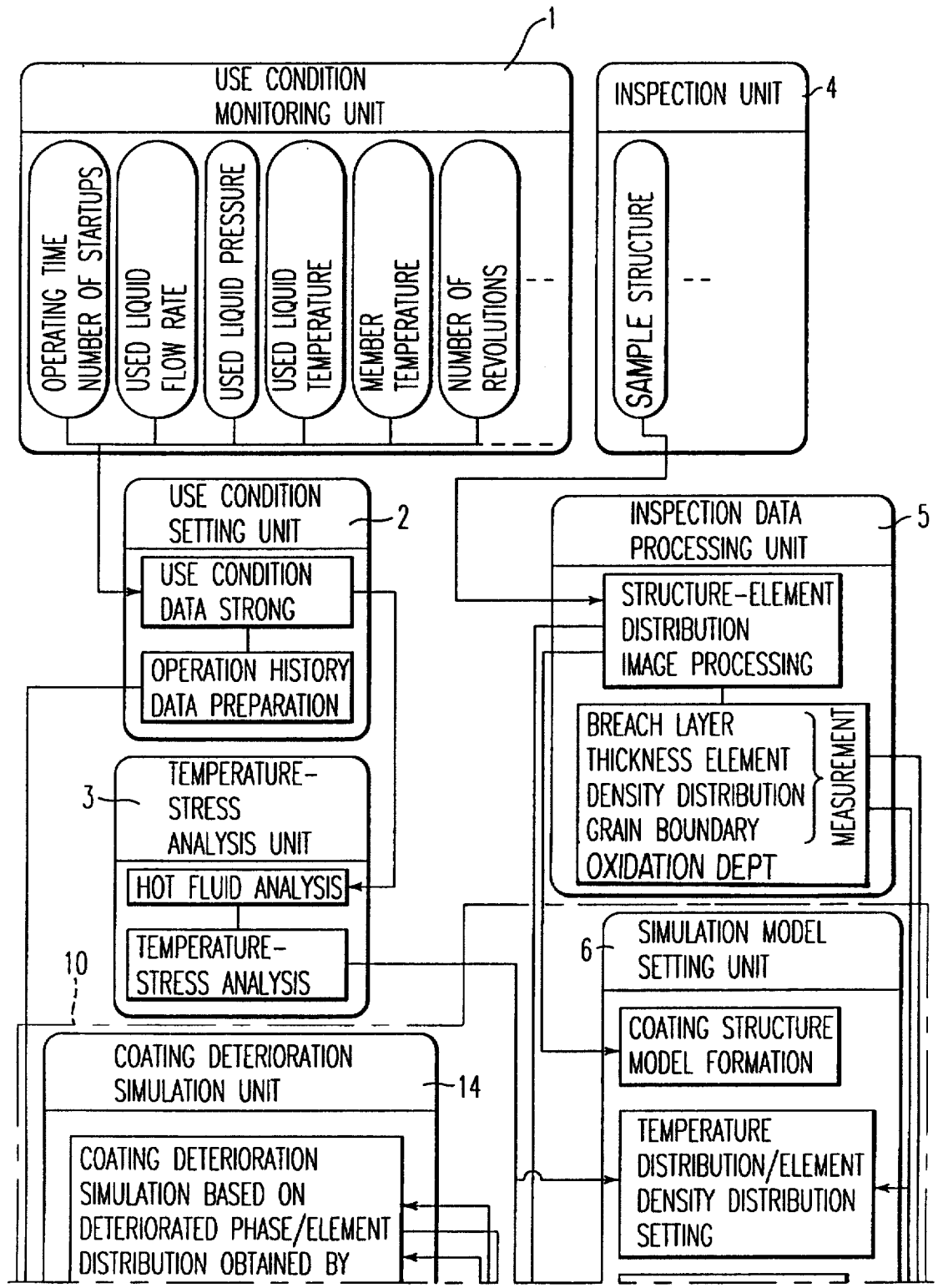
FIG. 16 is a diagram of the mutual relation between operations of the deterioration/damage prediction apparatus shown in FIG. 15.
Figure 16B:
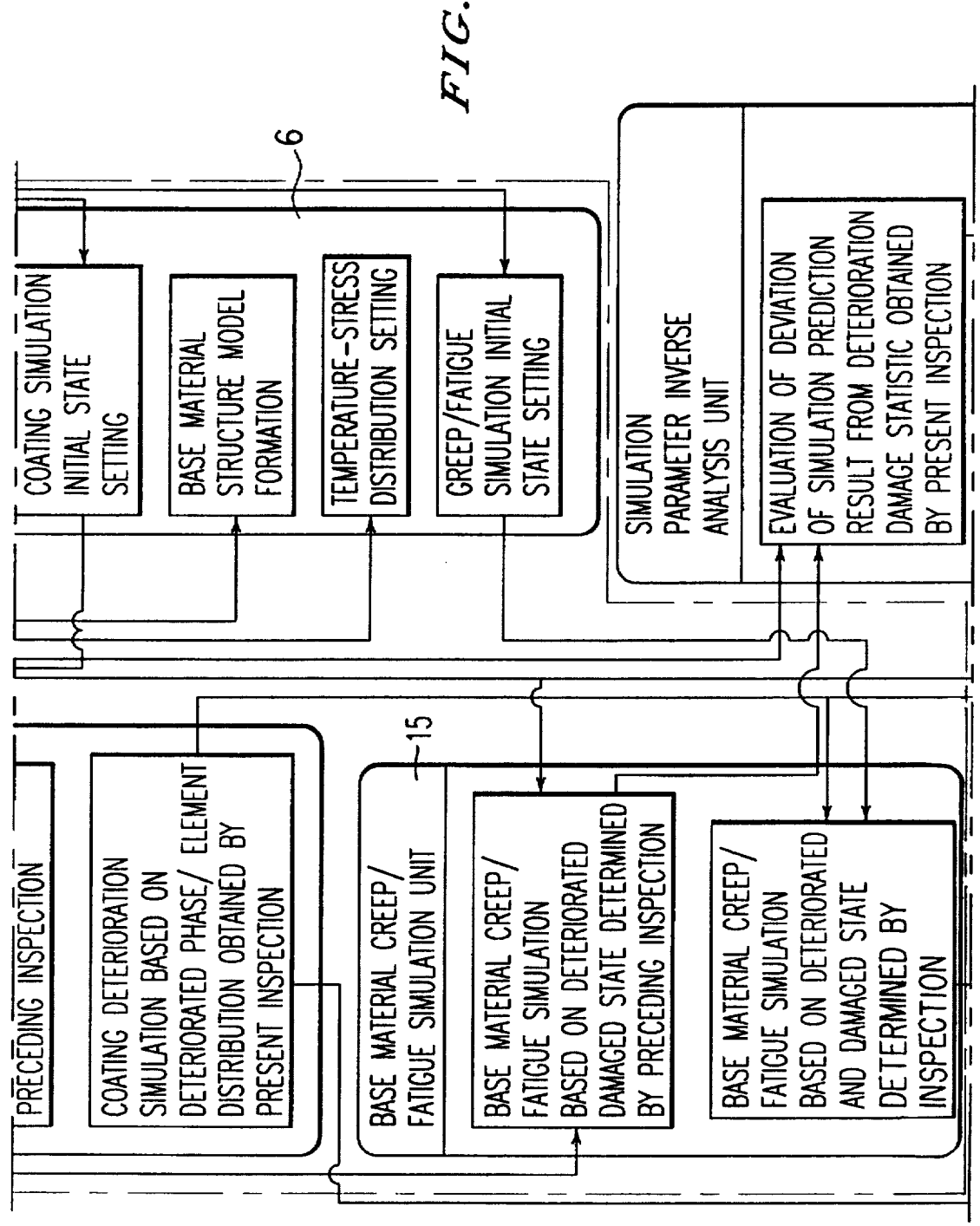
Figure 16C:
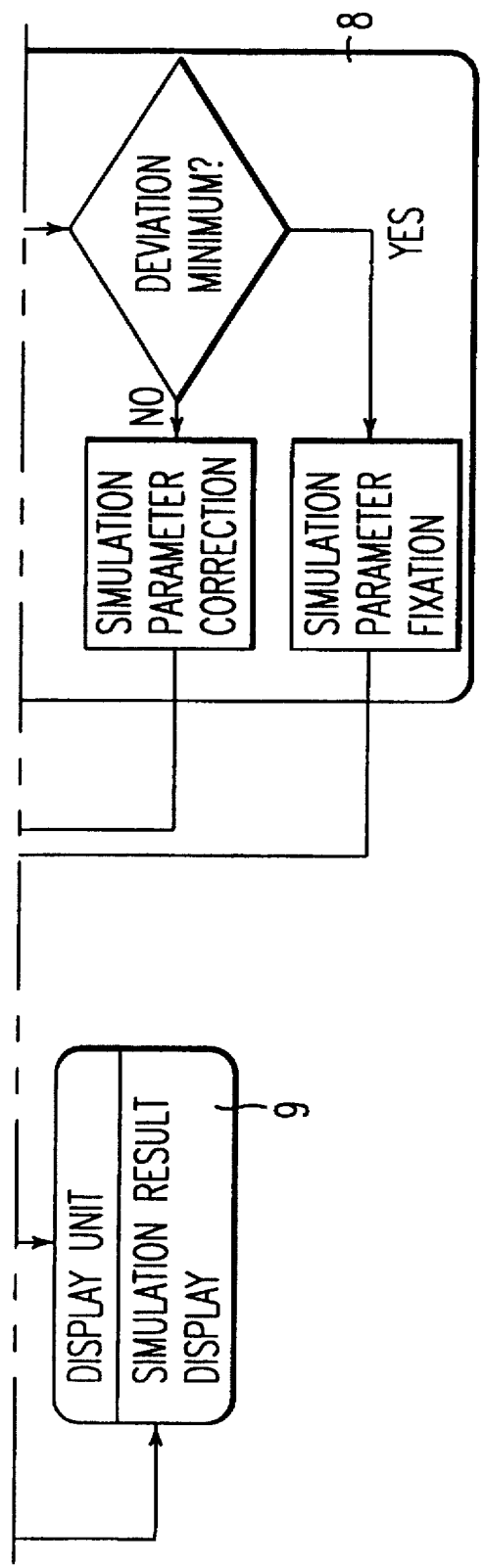

The operation of this structural member deterioration/damage prediction apparatus will be described with reference to FIG. 16.

The deterioration/damage prediction apparatus detects various conditions of use a structural member during operation through various sensors attached to the structural member. Signals representing the detected various use conditions during operation (e.g., the operating time, the number of startups, the flow rate, pressure and temperature of a fluid used, the temperatures of portions of the structural member, and the number of revolutions) are monitored by the use condition monitoring unit 1. The detected use condition signals are stored as use condition data in the use condition setting unit 2. The use condition setting unit 2 prepares, as operation history data, a history with respect to the operating time and the number of startups and so on of the use condition data.

On the other hand, in the temperature-stress analysis unit 3, hot fluid analysis and temperature-stress analysis based on hot fluid analysis are performed with the use condition data used as boundary conditions. These analyses are achieved by using the finite element method or the boundary element method.

Specifically, in this embodiment, the inspection unit 4 measures a breach phase, i.e., a deteriorated phase generated in an internal base material portion by diffusion of aluminum (Al) from a coating layer, and damage in the base material which may result in creep/fatigue cracks among various factors of deterioration and damage in the structural member. To do so, a sample is selected from a group of the same parts, a cross section from the coating and the base material is observed with a microscope and an element distribution is observed by X-ray diffraction method or the like. Further, means for non-destructive detection of a deteriorated phase in a surface layer may be used if necessary.

Figure 17:
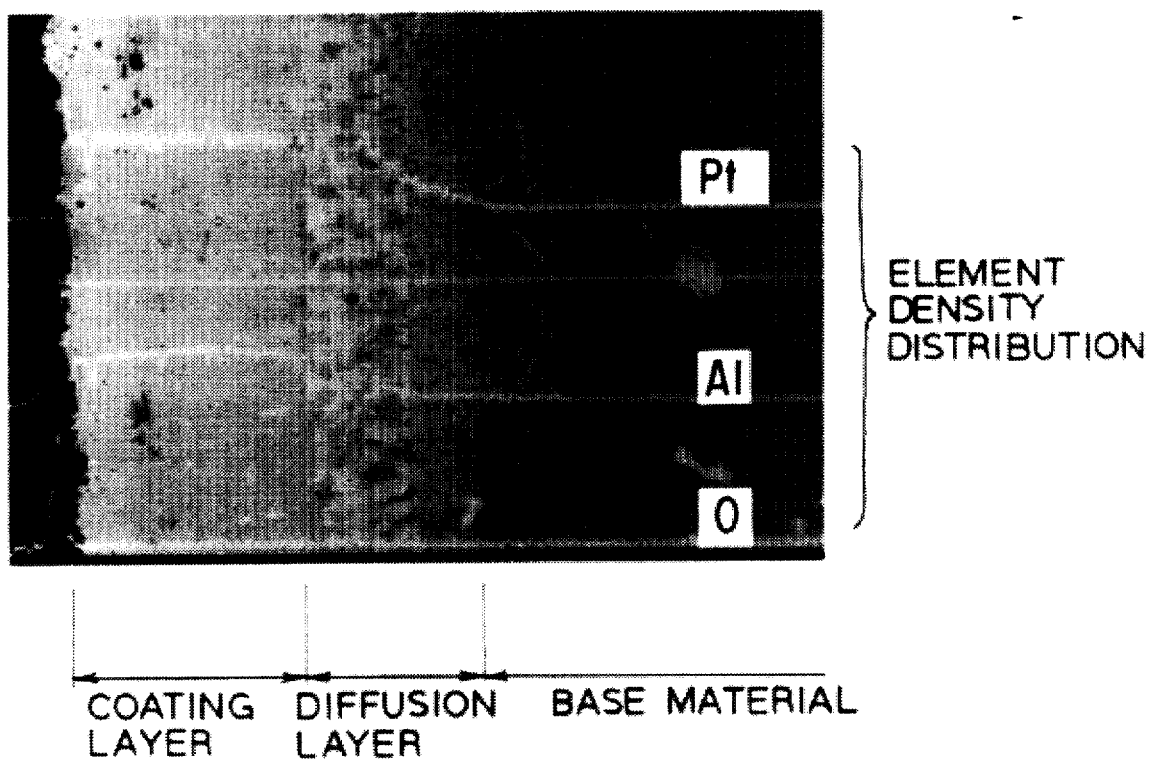
FIG. 17 is a diagram of an example of element analysis by microscopic observation of the metallic structure of a coated moving blade which is a structural member of a gas turbine.

Information on the deteriorated phase structure, the base material structure and the distribution of an element such as Al measured by the inspection unit 4 is processed by an image processor to form numerical data. For example, FIG. 17 shows a result of observation with a scanning tunnel type electronic microscope and element distribution analysis of a structural member which is a gas turbine moving blade member formed of a Ni-base super alloy precision-cast base material coated with Pt–Al. In this case, numerical data is formed from the thickness of a region where a needle-like breach phase which is a brittle compound of Al and Ni is generated, an element density distribution, the depth of a grain boundary oxide in the base material, a minute crack distribution, and crystal grain boundary void distribution.

Figure 18A:
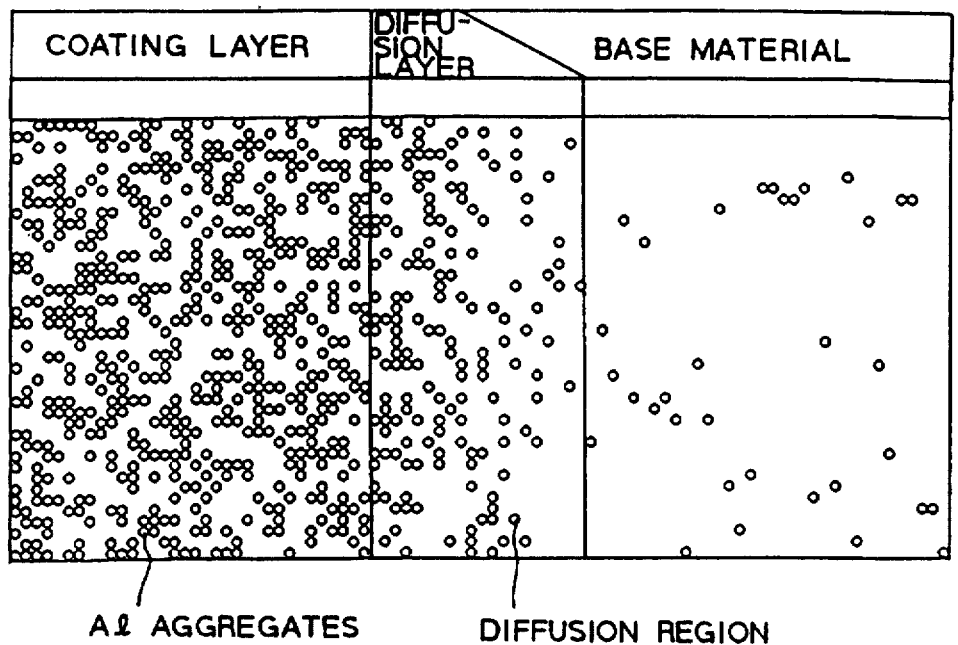
FIGS. 18(A) and 18(B) are diagrams of a coated structure model.
Figure 18B:
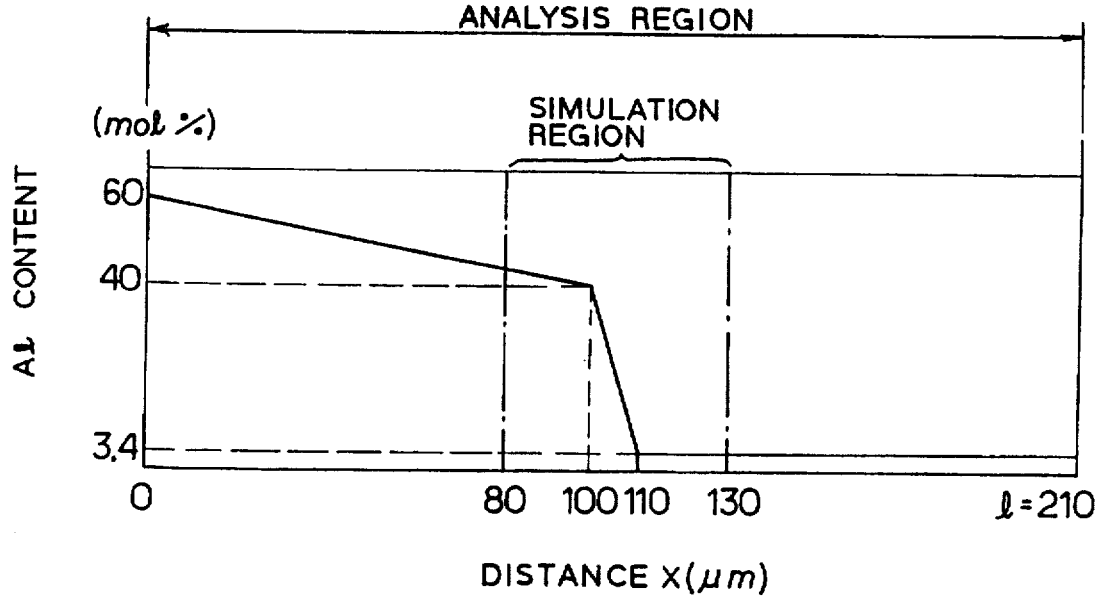

On the other hand, to prepare a coating structure model in the simulation model setting unit 6, the thicknesses of the coating layer, the diffusion layer and the base material of the object are set so as to coincide with a statistical distribution in the measurement result obtained by the inspection data processing unit 5, as shown in FIGS. 18(A) and 18(B). In this coating structure model, a temperature distribution obtained in temperature-stress analysis unit 3 and the element density distribution of Al are set numerically and aggregates of Al in each layer having a certain size are distributed probabilistically in accordance with the element density distribution obtained in the inspection data processing unit 5, thereby setting an initial state of coating simulation.

Next, in the coating deterioration simulation unit 14, coating deterioration simulation is performed by a process described below, with the breach phase thickness and the element distribution at the preceding inspection time used as an initial state.

It is well known that the element diffusion speed complies with the Fick's second law. Then, the Al diffusion speed can be expressed in accordance with this law by the following equation:

$$\partial C_{Al}/\partial t = \partial/\partial x\, (D\partial C_{Al}/\partial x) \tag{8}$$

where $C_{Al}$: average Al density t: operating time

D: diffusion coefficient x: distance from the surface.

In the model region shown in FIGS. 18(A) and 18(B), Al aggregates are irregularly placed by generating random numbers, assuming that the probability of the existence of Al aggregates is equal to the Al density. The amount of movement of Al is obtained by numerically calculating the equation (8). Assuming that Al aggregates move when the Al movement amount exceeds a certain value, moving Al aggregates and the direction of movement are determined with random numbers. With respect to the generation of a deteriorated phase, it is assumed that a breach phase is formed when a certain number of Al aggregates connect to each other by the movement of Al aggregates.

Figure 19:
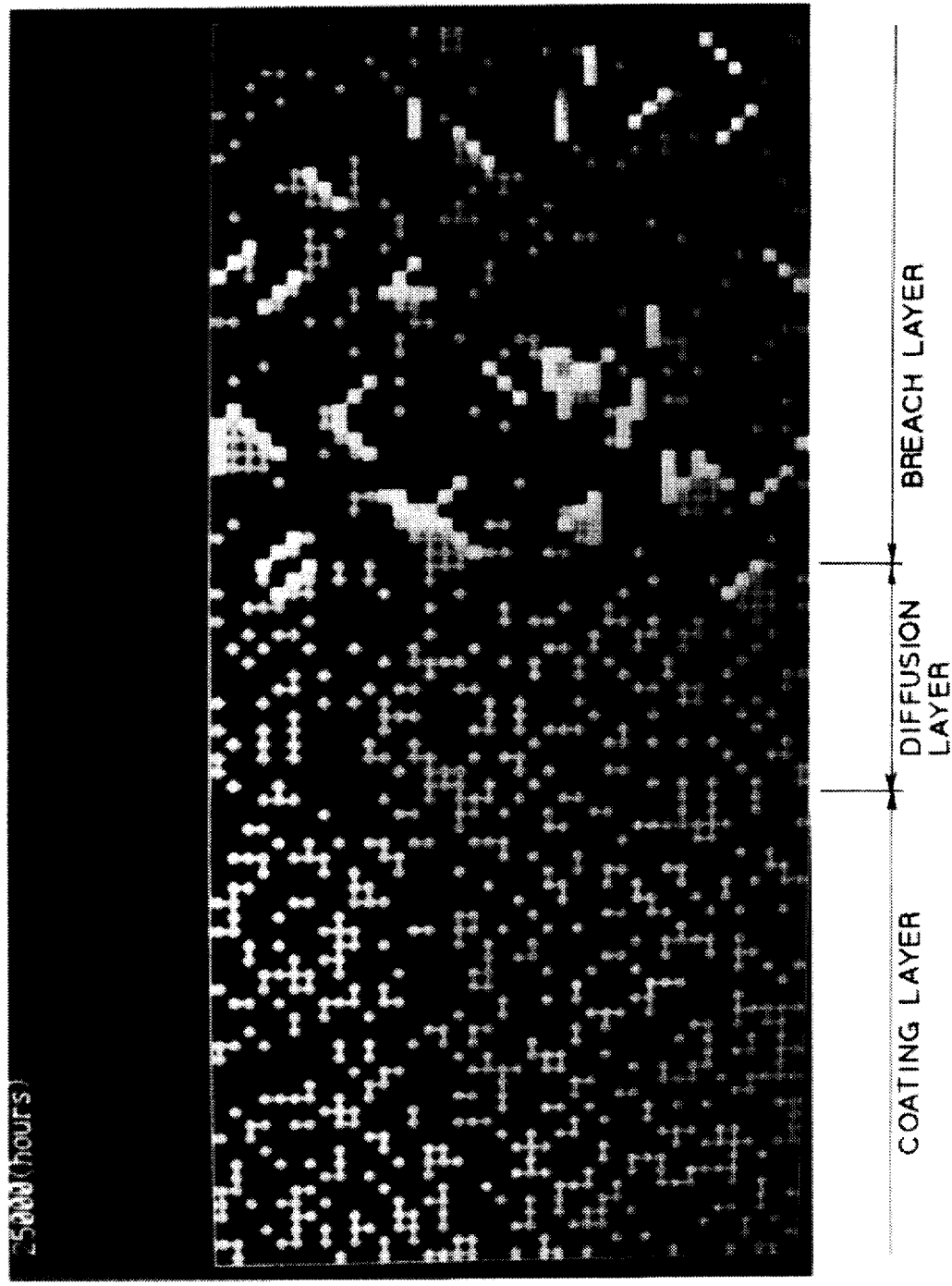
FIG. 19 is a diagram of an example of coating deterioration simulation.
Figure 20:
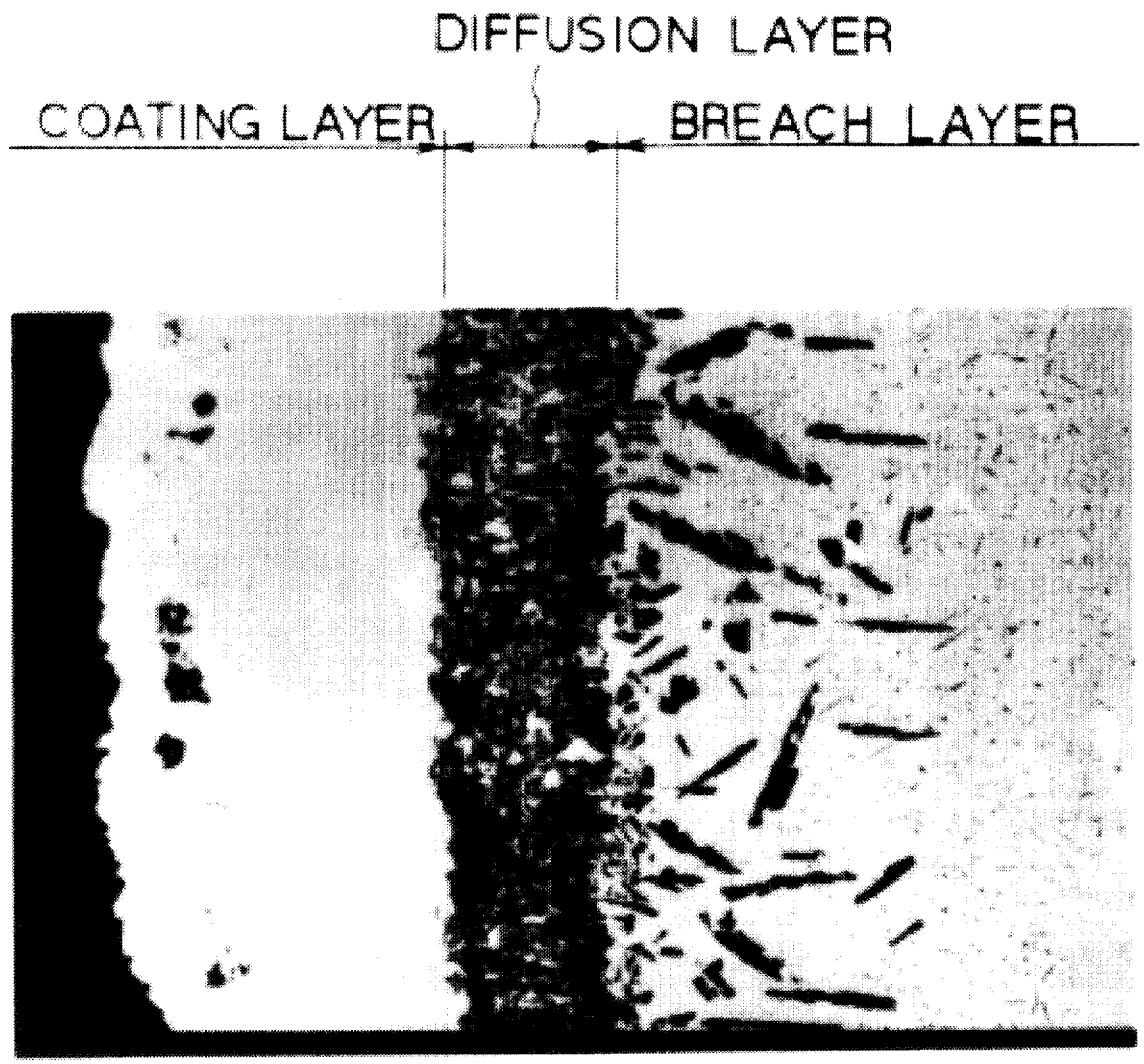
FIG. 20 is a diagram of generation of a deteriorated phase in a coated moving blade which is a structural member of a gas turbine.
Figure 21:
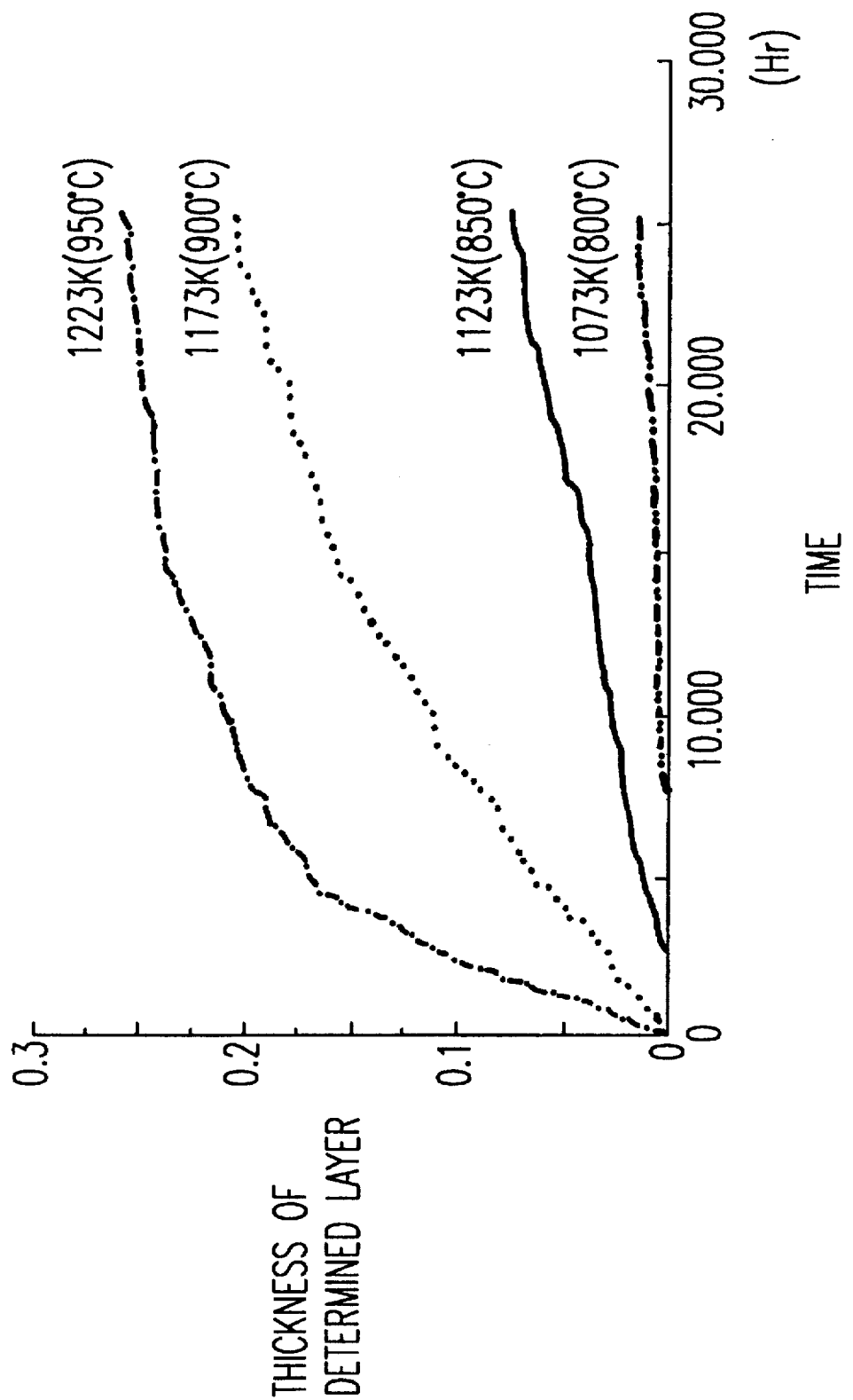
FIG. 21 is a graph showing curves indicating changes in the deteriorated phase thickness obtained by the coating deterioration simulation.

FIG. 19 shows an example of coating deteriorated phase generation simulation at the present inspection time performed in this manner. The result of simulation coincides satisfactorily with the result of a structure examination of an actual member shown in FIG. 20. The thickness of the deteriorated phase is increased monotonically with respect to time, as shown in FIG. 21, and larger absolute values are exhibited with respect to higher temperatures.

On the other hand, in the simulation parameter inverse analysis unit 8, the difference between the values of constants $\{\gamma_S, \beta_S, \alpha_S\}$ when the coating deteriorated phase thickness at the present inspection time obtained by the above-described simulation is approximated to the distribution form of the equation (2) and present inspection data $\{\gamma_I, \beta_I, \alpha_I\}$ obtained in the inspection data processing unit 5 is calculated as a deviation.

The deviation $\{\delta\alpha, \delta\beta, \delta\gamma\}$ is expressed by the following equation:

$$\{\delta\alpha, \delta\beta, \delta\gamma\} = \{\alpha_S - \alpha_I, \beta_S - \beta_I, \gamma_S - \gamma_I\} \tag{9}$$

A function $W(T, D, Pb)$ of the damage parameters is expressed by $$W(T, D, Pb) = \Sigma\{\omega_1 \cdot \delta\gamma^2 + \omega_2 \cdot \beta^2 + \omega_3 \cdot \delta\alpha^2\} \quad (10)$$

where

T: temperature

Pb: breach phase generation probability $\Sigma$: sum in each simulation $\omega_1, \omega_2, \omega_3$: weighting functions.

T, D and Pb such that the function W(T, D, Pb) of the damage parameters is minimum or least are searched for and obtained by repeated calculations, and corresponding damage parameter values are fixed as final values.

When the simulation parameters (damage parameters) are fixed, the operation of the coating deterioration simulation unit 14 is performed again for future crack generation/growth simulation with the state of the coating layer at the present inspection time used as an initial state. The result of this simulation is displayed on the display unit 9.

Next, creep/fatigue simulation of the base material of the structural member is performed.

Figure 22:
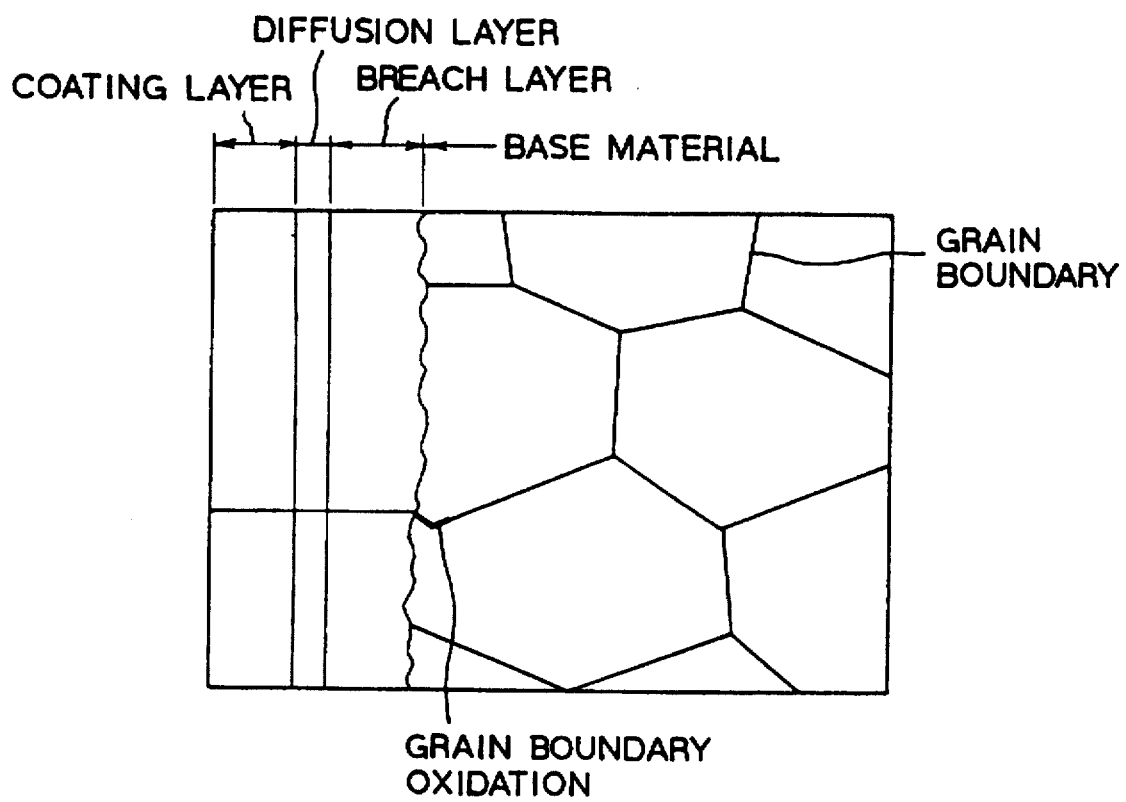
FIG. 22 is an enlarged diagram of a simulation model of the structure member base material.

In the simulation model setting unit 6, a simulation model having the creep/fatigue state of the base material at the preceding inspection time as an initial state is used. However, it is known that a polycrystalline structure in the base material structure largely influences the generation of creep/fatigue cracks. Then, the geometrical configuration of crystal grain boundaries is represented by a set of line segments such as those shown in FIG. 22, and oxidation of crystal grain boundaries is simulated as minute cracks, if oxidation has advanced to internal crystal grain boundaries. Further, the temperature-stress distribution obtained in the temperature-stress analysis unit 3 is given to the simulated simulation region.

Next, resistance R of the material against the generation and growth of cracks and a parameter relating to crack generation/growth drive force F, such as the temperature-stress distribution obtained from the temperature-stress analysis unit 3, are assumed. A crack generation resistance RI and a crack growth resistance RG of the material cannot be set as single constants because they are influenced by various composite factors. At this stage, therefore, supposed values are set. This point is particularly considered in setting with respect to creep, because damage is concentrated on grain boundaries.

An initial state of the crack distribution in the simulation model is set by using random numbers so as to coincide with the statistical distributions of the oxide layers and minute cracks at the preceding time obtained by the inspection data processing unit 5. Crack generation/growth is determined by numerical simulation on the basis of the operation history (the number of startups, the operating time, and so on) from the preceding inspection time to the present inspection time prepared in the use condition setting unit 2. The generation and growth of cracks are subject to a damage function D represented by the following equations:

$$\text{Crack generation } D_{I,\,i} = D_{I,\,i-1} + \partial D_I(R, F)/\partial t \cdot \Delta t \quad (11)$$

$$\text{Crack growth } D_{G,\,i} = D_{G,\,i-1} + \partial D_G(R, F)/\partial t \cdot \Delta t \quad (12)$$

where $D_{I,\,i}$: Crack generation damage function at i stage $D_{G,\,i}$: Crack growth damage function at i stage t: time or number of times $\Delta t$: an increase in time or number of times between from i−1 stage to i stage $D_I(R,F) = 1 - \exp(-t/b_I)^{m_I}$ $b_I = R_{C,I}/F_{C,I}$ (in the case of creep)

$R_{f,I}/F_{f,I}$ (in the case of fatigue)

$D_G(R, F) = 1 - \exp(-t/b_G)^{m_G}$ $b_G = R_{C,G}/F_{C,G}$ (in the case of creep)

$R_{f,G}/F_{f,G}$ (in the case of fatigue)

Assuming that with respect to the process of crack generation/growth from the void generation/growth/union due to creep and the process of crack generation/growth due to fatigue, the values of the above damage function D are equal to the probabilities of occurrence of these phenomena, simulation is performed with respect to each point of the object region by using random numbers.

In the simulation parameter inverse analysis unit 8, the crack length distribution is converted into a statistic by the equation (2) from the state of crack distribution prediction at the present inspection time obtained by the above-described simulation, and the difference between the values of constants 55 $\{\alpha'_s, \beta'_s, \gamma'_s\}$ of the converted values and present inspection data $\{\alpha'_I, \beta'_I, \gamma'_I\}$ obtained in the inspection data processing unit 5 is calculated as a deviation.

That is, constants $\{\delta\alpha', \delta\beta', \delta\gamma'\}$ are expressed by the following equation:

$$\{\delta\alpha', \delta\beta', \delta\gamma'\} = \{\alpha'_s - \alpha'_I, \beta'_s - \beta'_I, \gamma'_s - \gamma'_I\} \quad (13)$$

Function W(R, F, D) of damage parameters is expressed by the following equation:

$$W(R, F, D) = \Sigma\{\omega'_1 \cdot \delta\alpha^2 + \omega'_2 \cdot \delta\beta'^2 \omega'^3 \cdot \delta\gamma^2\} \quad (14)$$

where $\Sigma$: sum in each simulation $\omega'_1, \omega'_2, \omega'_3$: weighting functions.

R, F and D such that the function W(R, F, D) of the damage parameters is minimum or least are searched for and obtained by repeated calculations, and corresponding parameter values are fixed as final values.

Figure 23A:
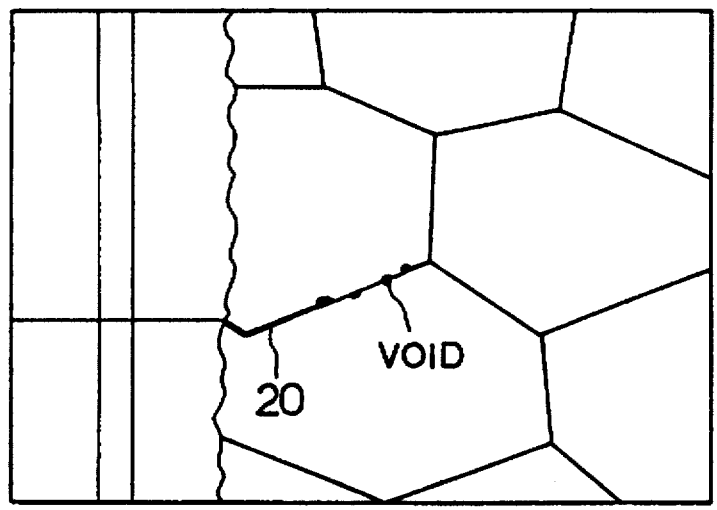
FIGS. 23(A) to 23(C) are deterioration/damage prediction display images obtained by simulation of the coating base material.
Figures 23B, 23C:
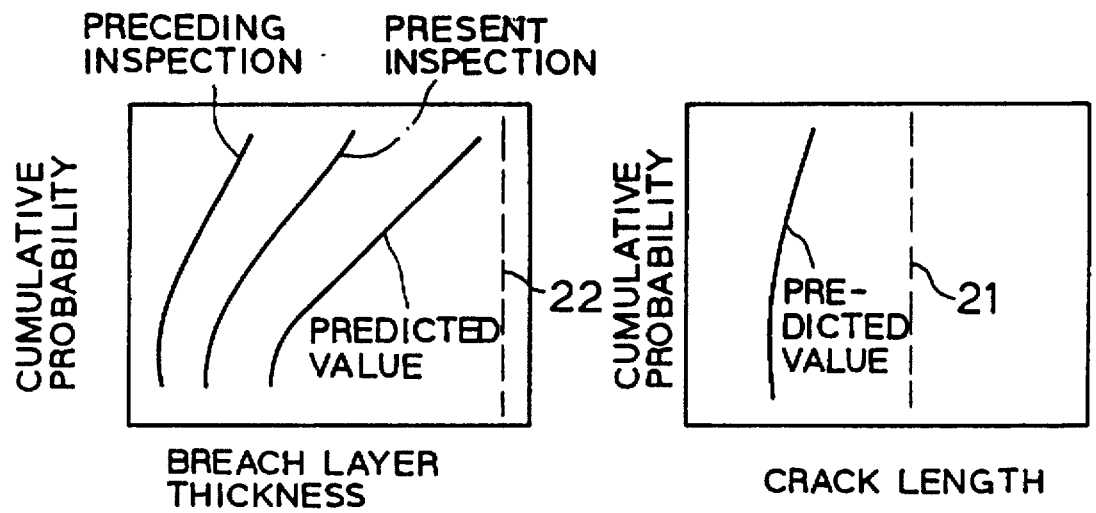

When the simulation parameters are fixed, future crack generation/growth simulation is performed in the base material creep/fatigue simulation unit 15 with the crack distribution state at the present inspection time used as an initial state. The result of this simulation is displayed on the display unit 9. FIGS. 23(A) to 23(C) show examples of display on the display unit 9. An image of the crack distribution obtained by simulation as shown in FIG. 23(A), changes in crack length distribution such as those shown in FIG. 23(B) and changes in breach layer thickness such as those shown in FIG. 23(C) are displayed on the display unit 9. With respect to changes in crack length and breach layer thickness distributions, allowable limits 21 and 22 are simultaneously indicated and a guidance for taking necessary measures is also shown.

In this embodiment, it is possible to form a deterioration/damage model having a close similarity to the actual state by using inspection results and to accurately predict a deterioration and damage in a structural member, even if the construction of a deterioration/damage prediction model is difficult because factors which determine the advancement of the deterioration and damage are complicated or non-linear and because the deterioration/damage order is an important influence factor.

Figure 24:
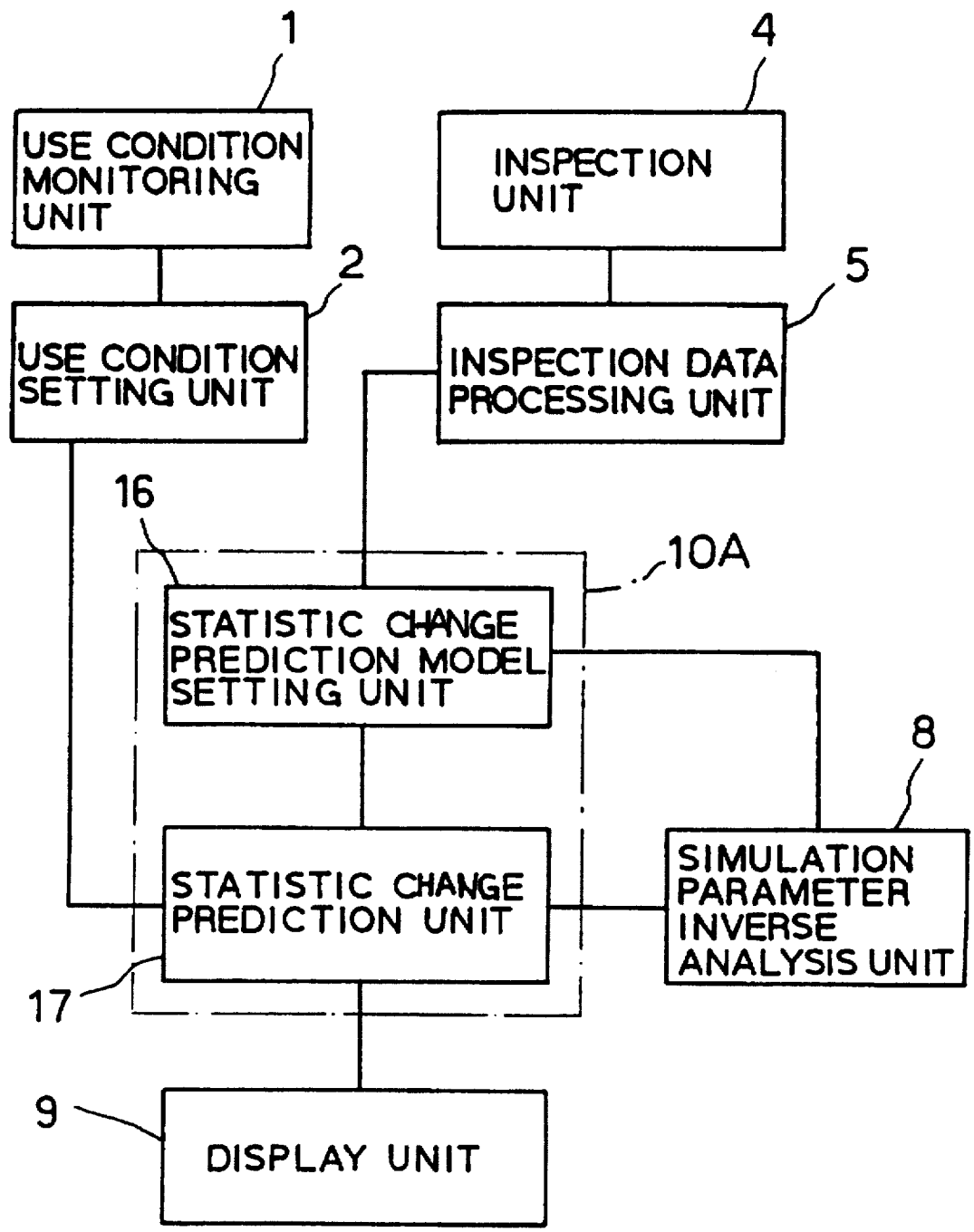
FIG. 24 is a diagram of the configuration of a structural member deterioration/damage prediction apparatus in accordance with a fourth embodiment of the present invention, showing an example of an application to a deterioration/damage prediction based on an inspection result statistic.

FIG. 24 shows a structural member deterioration/damage prediction apparatus in accordance with a fourth embodiment of the present invention. The deterioration/damage prediction apparatus of this embodiment is an example of an arrangement for predicting a deterioration and damage of a structural member on the basis of a statistic obtained as an inspection result.

This structural member deterioration/damage prediction apparatus has a use condition motoring unit 1 for monitoring conditions of use of a prime mover or the like, and an inspection unit 4 for inspecting a deterioration and damage in a structural member.

The use condition monitoring unit 1 is connected to a statistic change prediction unit 7 through a use condition setting unit 2. The inspection unit 4 is connected to an inspection data processing unit 5 which is connected to a statistic change prediction model setting unit 16. The statistic change prediction model setting unit 16 corresponds to the simulation model setting unit shown in FIG. 1.

The statistic change prediction model setting unit 16 is connected to the statistic change prediction unit 17 to form a change predictor 10A, while the use condition setting unit 2 is connected to the statistic change prediction unit 17. The statistic change prediction unit 17 corresponds to the deterioration/damage simulation unit 7 shown in FIG. 1. The statistic change prediction unit 17 is connected again to the statistic change prediction model setting unit 6 through a simulation parameter inverse analysis unit 8. The statistic change prediction unit 17 is also connected to a display unit 9 to display processing results on the display unit 9.

Figure 25B:
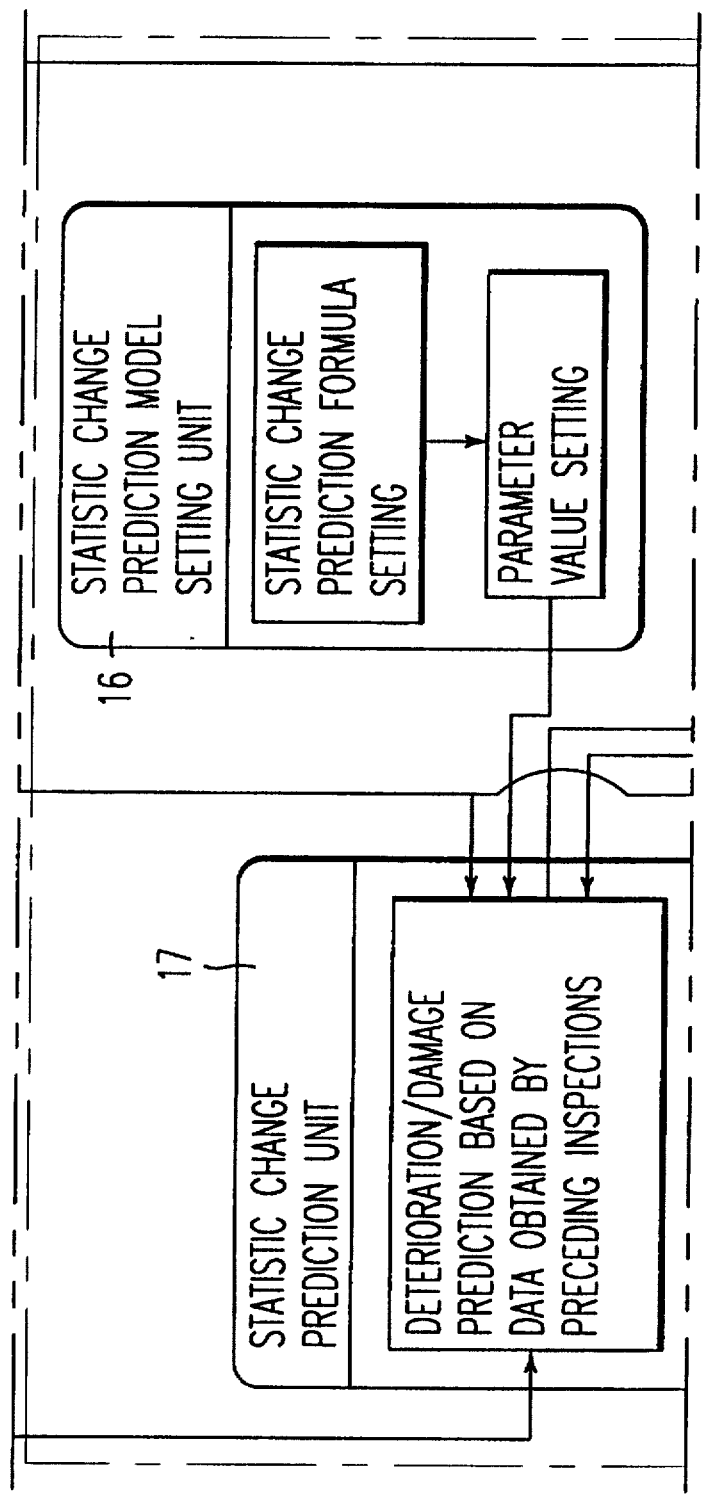
FIG. 25 is a diagram of the mutual relation between operations of the deterioration/damage prediction apparatus shown in FIG. 24.
Figure 25C:
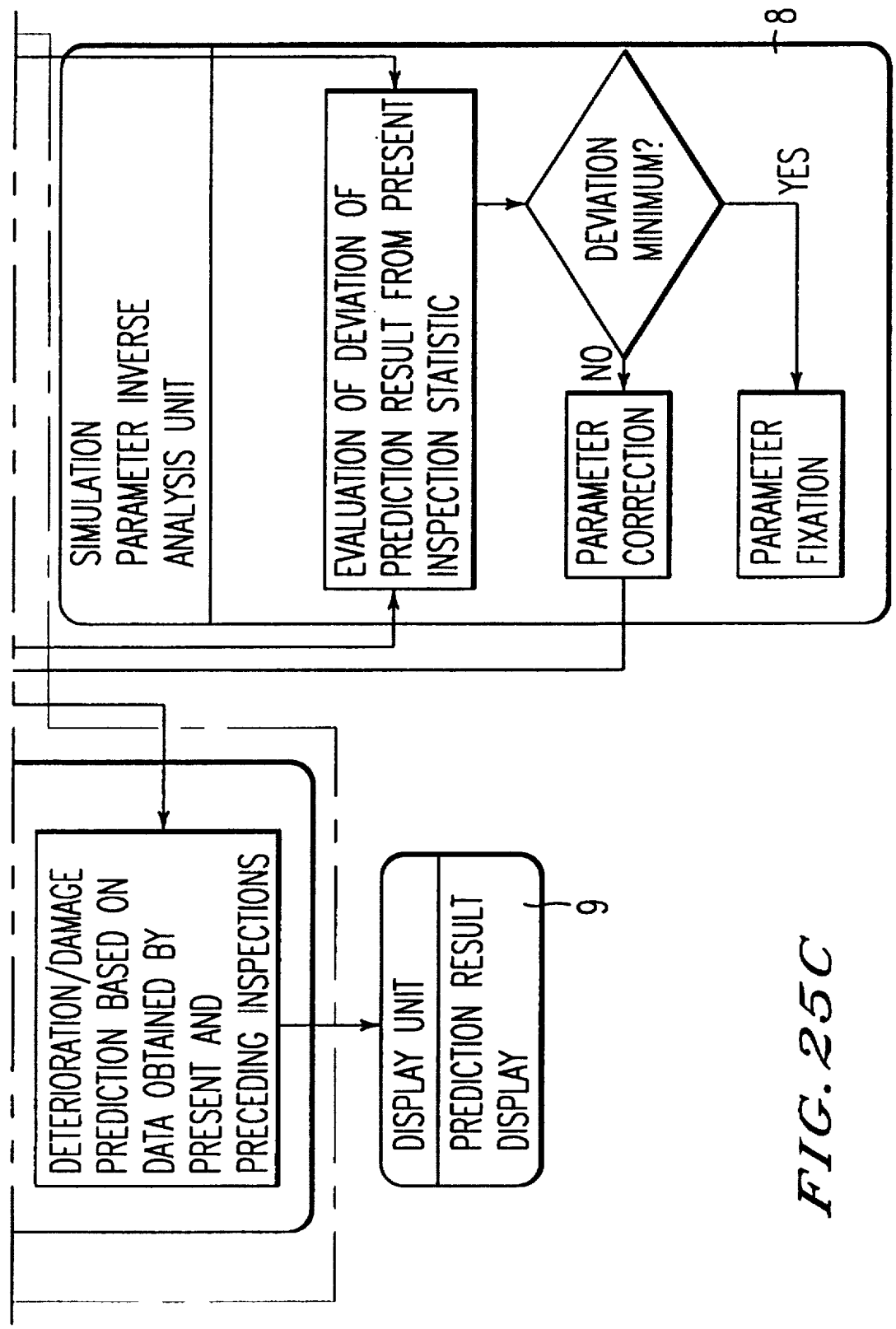

The operation of this deterioration/damage prediction apparatus will be described with reference to FIG. 25.

This deterioration/damage prediction apparatus detects conditions of use, such as the operating time and the number or startups, of a structural member of a prime mover or the like through detectors (sensors) attached to the structural member. These use conditions are monitored by the use condition monitoring unit 1. Signals representing the detected use conditions are stored as use condition data in the use condition setting unit 2. The use condition setting unit 2 prepares a history of the use condition data as operation history data.

On the other hand, the inspection unit 4 measures cracks and deformations as deteriorations and damage in the structural member, and measures a metallic structure, hardness and other factors through a replica. An example of prediction with respect to cracks caused in a stationary blade which is a structural member of a gas turbine will be described.

Inspection data obtained by measurement with the inspection unit 4 is supplied to and stored in the inspection data processing unit 5. Numerical data such as crack lengths is processed by statistical processing to obtain a result such as that shown in FIG. 6. In the statistic change prediction model setting unit 16, a change in a statistic $\{\alpha, \beta, \gamma\}$ is represented as a monotonic increase function of the operating time or the number of startups, if three-parameter Weibull distribution approximation of crack length represented by an optimal approximation formula (2) is used. A group of coefficient values $\{A\}, \{B\}$, and $\{C\}$ in this statistic change prediction formula are regarded as parameters and are set as assumed values here.

On the other hand, in the simulation parameter inverse analysis unit 8, the difference between the statistic at the present inspection time obtained in the statistic change prediction unit 17 and the statistic at the present inspection time obtained in the inspection data processing unit 5 is calculated as a deviation. That is, if $\{\delta\alpha, \delta\beta, \delta\gamma\}$ are defined by the equation (6), a function $W(\{A\}, \{B\}, \{C\})$ of the damage parameters is expressed by the same equation as the equation (7). $\{A\}, \{B\}$, and $\{C\}$ such that the function W of the damage parameters is minimum or least are searched for and obtained by repeated calculations, and corresponding parameter values are fixed as final values.

Figure 26A:
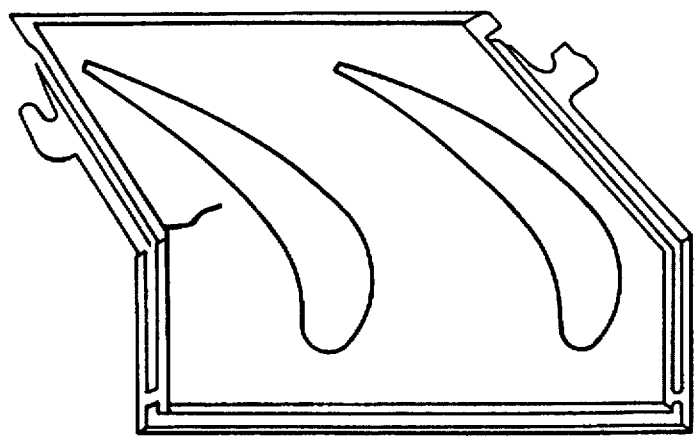
FIGS. 26(A) and 26(B) are schematic diagrams of examples of display of deterioration/damage prediction results obtained by the deterioration/damage prediction apparatus shown in FIG. 24.
Figure 26B:
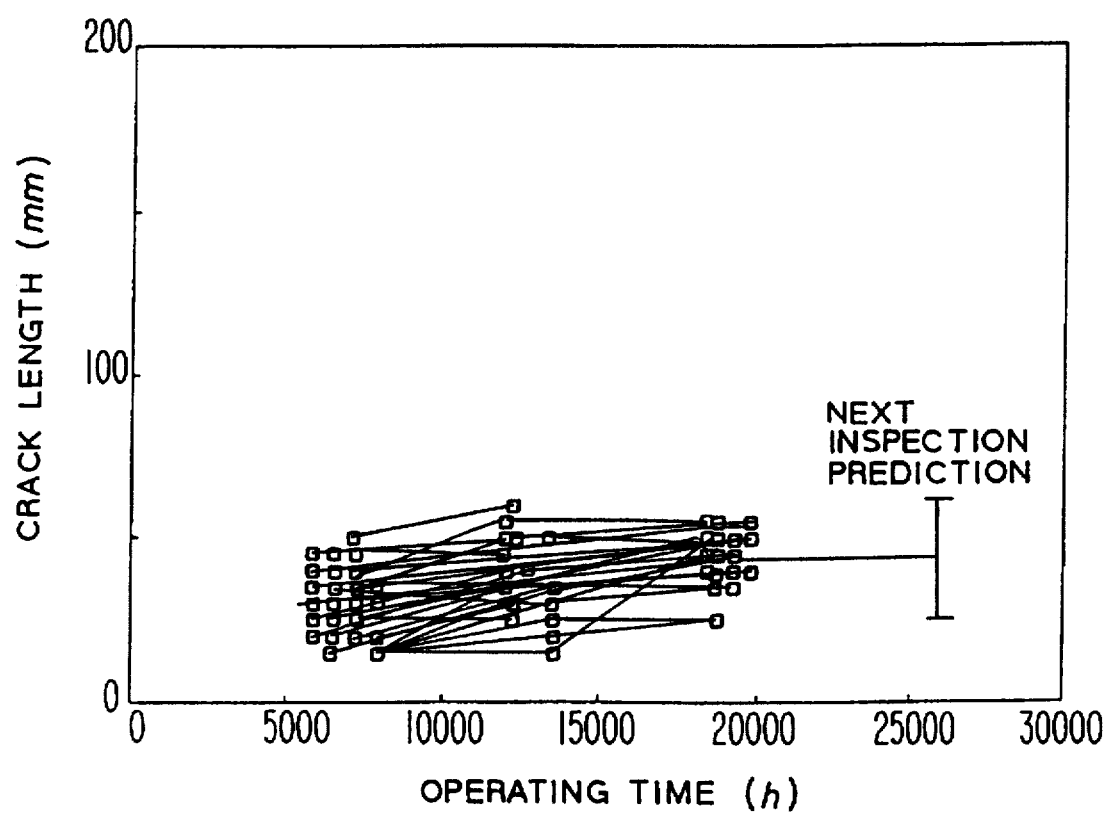
Figure 27:
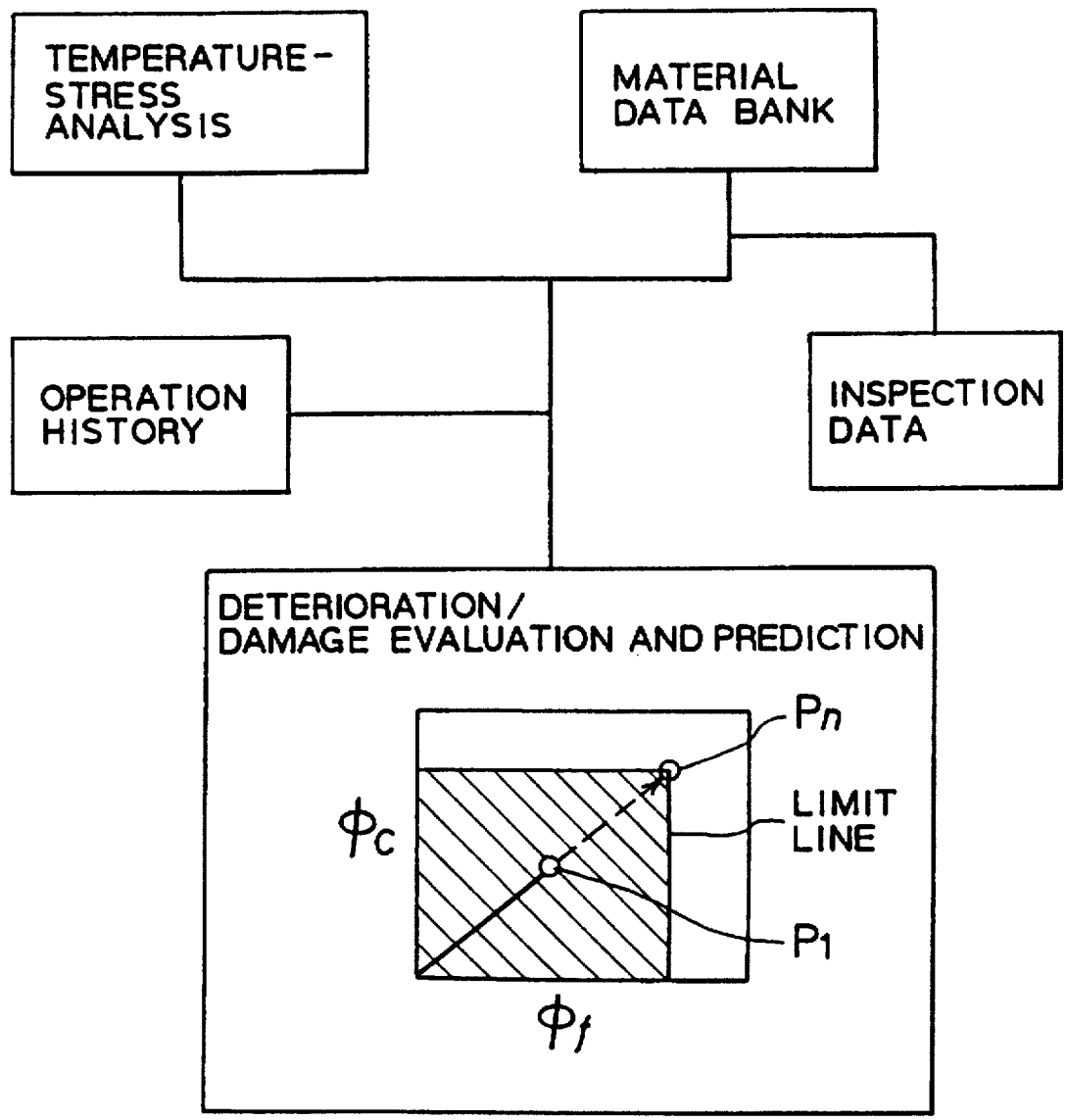
FIG. 27 is a diagram of a conventional method of evaluating damage in a structural member.

When the parameters are fixed, the operation in the statistic change prediction unit 17 is performed again for future crack length statistic prediction on the basis of inspection data obtained previously and at the present inspection time, and results of this prediction are displayed as shown in FIGS. 26(A) and 26(B). In this case, crack growth data obtained previously and at the present inspection time, and a future crack growth prediction line are shown.

In this embodiment, it is possible to determine a deterioration/damage prediction formula having close similarity to the actual state by using inspection results and to accurately predict a deterioration and damage in a structural member, even if factors which determine the advancement of the deterioration and damage are complicated or non-linear, the construction of a deterioration/damage prediction model is difficult and there is no analyzed use condition data such as temperature-stress analysis data or use condition analysis is difficult to perform.

In accordance with the present invention, as described above, conditions of use of a structural member are monitored by the use condition monitoring unit, a deteriorated and damaged state of the structural member is inspected by the inspection unit, and the simulator forms a model of a deterioration and damage in the structural member on the basis of the structural member use conditions and the result of inspection at the preceding time, and simulates the deterioration and damage in the structural member on the basis of the deterioration/damage model. The simulation model made by the simulator is compared with the result of present inspection of the structural member by an inverse analysis unit to be corrected. The corrected model is sent to the simulator.

The simulator is arranged to predict a future deterioration/damage in the structural member by using the corrected simulation model and the present inspection result. It is therefore possible to construct a deterioration/damage model having a close similarity to the actual state by using the inspection result and by the inverse-problem analysis method and to accurately predict the deterioration and damage in the structural member, even if the deterioration/damage phenomena of the structural member are complicated and the construction of a deterioration/damage model is difficult.

Also, the apparatus is arranged so that the simulation model is corrected every time from the use conditions of the structural member and the inspection result, and a future deterioration/damage in the structural member is predicted by using the corrected simulation model and the present (latest) inspection result, even if the deterioration and damage in the structural member are caused under complex factors, e.g., a material structure factor, a temperature-stress distribution factor, an environmental corrosion factor and damage interference factor, such that the advancement of deterioration and damage is non-linear and complicated. The deterioration/damage prediction accuracy is thereby improved and, accordingly, the life of the structural member can be predicted accurately.

What is claimed is:

1. A method of predicting deterioration and damage in a structural member operated under a high temperature condition for a long period of time, the method comprising the steps of:

inspecting information regarding a number, position, shape, and length of micro cracks existing in the structural member;

forming a structural model of a set of lattice points and providing said information to the structural model as respective lattice points;

providing the respective lattice points with material resistances against various operating conditions such as temperature, stress, strain, crack initiation and crack growth as information, the material resistances being previously calculated in accordance with operating conditions of said structural member;

determining crack initiation and growth occurring at respective lattice points at each time when operating conditions such as pressure and temperature of the structural member are changed during an operation period, the crack initiation and growth being determined on the basis of a calculation of a damage function which is defined as a function of stress, strain, and material resistances; and predicting an amount of time until a length of the crack growth will extend to a limit value by determining the crack growth due to coalescence of respective micro cracks.

2. A method of predicting deterioration and damage in a structural member operated under a high temperature condition for a long period of time, the method comprising the steps of:

inspecting information regarding a number, position, shape, and length of micro cracks existing in the structural member;

converting the information into numerical parameters of crack number, crack average length, and crack dispersion, and memorizing the numerical parameters;

presenting variation trends of the numerical parameters, with respect to a number of start/stop times or an operating time of the structural member, as an optimal approximation formula;

predicting future variation trends of the numerical parameters of crack number, crack average length, and crack dispersion on the basis of the optimal approximation formula;

predicting a maximum length or an overall length of a crack to be grown due to coalescence of the micro cracks, and setting the maximum length or the overall length of a limit value; and predicting an amount of time until a current crack length extends to the limit value and the structural member is brought to breakdown due to growth and coalescence of the micro cracks distributed in the structural member.

3. A method of predicting deterioration and damage in a structural member operated under a high temperature condition for a long period of time, wherein the prediction is performed by predicting an amount of time until the structural member is brought to breakdown due to increase of an injurious compound phase therein, the injurious compound phase being not formed at a manufacturing time of the structural member but then initiated and grown by diffusion and chemical combination of elements constituting the structural member to thereby cause micro-structural degradation, the method comprising the steps of:

inspecting information regarding a distribution of the elements constituting the structural member and temperatures of respective portions of the structural member;

forming a structural model of a set of lattice points and providing the information to the structural model as respective lattice points;

calculating initiation and growth of the injurious compound phase promoted by diffusion of the elements constituting said structural member, the calculation being performed in such a manner that diffusion rates of the elements at respective lattice points are irregularly distributed using random numbers and diffusion analysis;

displaying a geometrical shape and a distribution of the injurious compound phase on the lattice points of the structural model; and predicting an amount of time until the injurious compound phase extends to a critical state and the structural member is brought to breakdown due to micro-structural degradation of the structural member.

* * * * *